(12) United States Patent
Hobro et al.

(10) Patent No.: US 12,121,644 B2
(45) Date of Patent: Oct. 22, 2024

(54) PERFORMANCE MONITORING OF REGIONAL CITRATE ANTICOAGULATION

(71) Applicant: Gambro Lundia AB, Lund (SE)

(72) Inventors: Sture Hobro, Lund (SE); Jonas Alson, Lund (SE); Anders Nilsson, Södra Sandby (SE); Innas Forsal, Malmö (SE)

(73) Assignee: Gambro Lundia AB, Lund (SE)

( * ) Notice: Subject to any disclaimer, the term of this patent is extended or adjusted under 35 U.S.C. 154(b) by 690 days.

(21) Appl. No.: 17/311,874

(22) PCT Filed: Oct. 30, 2019

(86) PCT No.: PCT/EP2019/079721
§ 371 (c)(1),
(2) Date: Jun. 8, 2021

(87) PCT Pub. No.: WO2020/120004
PCT Pub. Date: Jun. 18, 2020

(65) Prior Publication Data
US 2022/0016325 A1 Jan. 20, 2022

(30) Foreign Application Priority Data
Dec. 11, 2018 (SE) .................................. 1851551-0

(51) Int. Cl.
*A61M 1/36* (2006.01)
*A61M 1/34* (2006.01)

(52) U.S. Cl.
CPC ........ *A61M 1/3672* (2013.01); *A61M 1/3434* (2014.02); *A61M 1/3437* (2014.02);
(Continued)

(58) Field of Classification Search
CPC .............. A61M 1/3672; A61M 1/3434; A61M 1/3437; A61M 1/342; A61M 2205/3334;
(Continued)

(56) References Cited

U.S. PATENT DOCUMENTS 9,039,647 B2    5/2015  Lannoy
2008/0015487 A1* 1/2008  Szamosfalvi ....... A61M 1/3413
                                               210/323.1
(Continued)

FOREIGN PATENT DOCUMENTS

CN    102309785 A    1/2012
CN    107617132 A    1/2018
(Continued)

OTHER PUBLICATIONS

International Search Report mailed Feb. 13, 2020—International Application No. PCT/EP2019/079721—4 Pages.
Written Opinion of the International Searching Authority mailed Feb. 13, 2020—International Application No. PCT/EP2019/079721—8 Pages.
Swedish Search Report mailed May 22, 2010—Swedish Application No. 1851551-0—9 Pages.

*Primary Examiner* — Philip R Wiest
*Assistant Examiner* — Matthew Wrubleski
(74) *Attorney, Agent, or Firm* — K&L Gates LLP

(57) ABSTRACT

A monitoring device operates to monitor regional citrate anticoagulation (RCA) in a blood treatment system which is configured to administrate citrate to an extracorporeal blood circuit (10) upstream of a dialyzer (11) during a treatment session. At consecutive time steps during the treatment session, the monitoring device obtains a current measurement value of systemic ionized calcium ($iCa_{SYS}$) or systemic total calcium ($Ca_{SYS}$), operates a predefined algorithm on the current measurement value to generate a current computation value that represents ionized calcium ($iCa_2$, $iCa_3$) in blood at a selected location (loc2, loc3) downstream or upstream of the dialyzer (11) in the extracorporeal blood circuit (10), and presents and/or evaluates the current com-
(Continued)

putation value for assessment of the regional citrate anticoagulation. The need for conventional blood sampling and blood analysis upstream and/or downstream of the dialyzer, e.g. during CRRT, is thereby reduced significantly.

26 Claims, 8 Drawing Sheets

(52) U.S. Cl.
CPC . *A61M 2205/3334* (2013.01); *A61M 2205/50* (2013.01); *A61M 2230/20* (2013.01)

(58) Field of Classification Search
CPC ...... A61M 2205/50; A61M 2205/3327; A61M 2230/20
See application file for complete search history.

(56) References Cited

U.S. PATENT DOCUMENTS

| | | | |
|---|---|---|---|
| 2011/0237996 A1* | 9/2011 | Kotanko | A61M 1/16 604/6.07 |
| 2011/0264025 A1 | 10/2011 | Lannoy | |
| 2014/0353251 A1 | 12/2014 | Kotanko et al. | |

FOREIGN PATENT DOCUMENTS

| | | |
|---|---|---|
| WO | WO 2010029401 A2 | 3/2010 |
| WO | WO 2010148194 A1 | 12/2010 |

* cited by examiner

| MS | PP | SP | CP |
|---|---|---|---|
| $Q_B$ | $H$ | $F_{CAL}$ | $EQ_{CaX}$ |
| $Q_D$ | $Alb$ | $k_0 A_Y$ | $iCIT$ |
| $Q_E$ | $HCO_3$ | $\alpha_Y$ | $iCa_{REF}$ |
| $Q_{PRE}$ | $pH$ | $\beta_0$ | $iP$ |
| $Q_{POST}$ | $W$ | $\beta_1$ | |
| $Q_{FIL}$ | $fpw$ | $\beta_2$ | |
| $Q_{PBP}$ | $V_D$ | $Ca_{REF}$ | |
| $D_{CIT}$ | $K_{BODY}$ | $CIT_{REF}$ | |
| | $G_{MET}$ | $K_C$ | |
| | $CIT_0$ | $K_{Ca}$ | |
| | | $CIT_{PBP}$ | |
FIG. 6
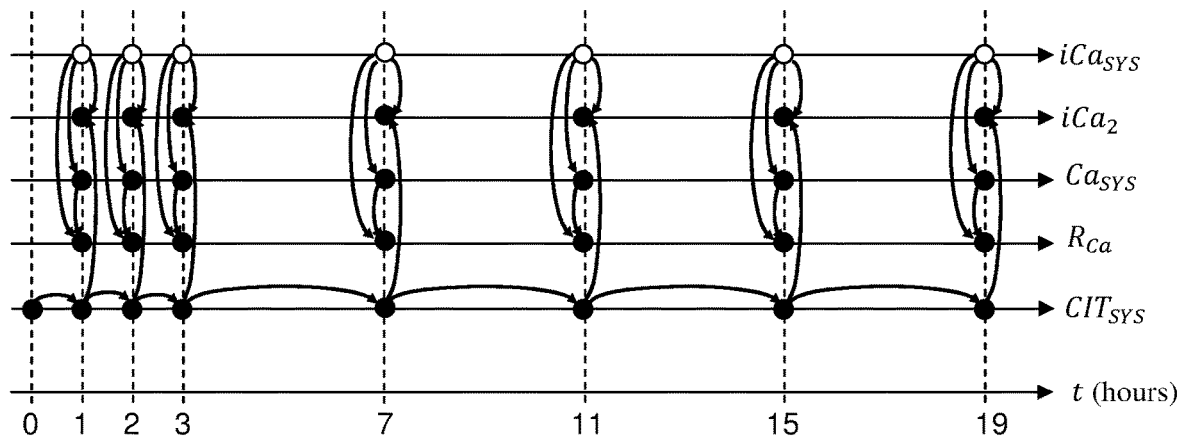
FIG. 8A
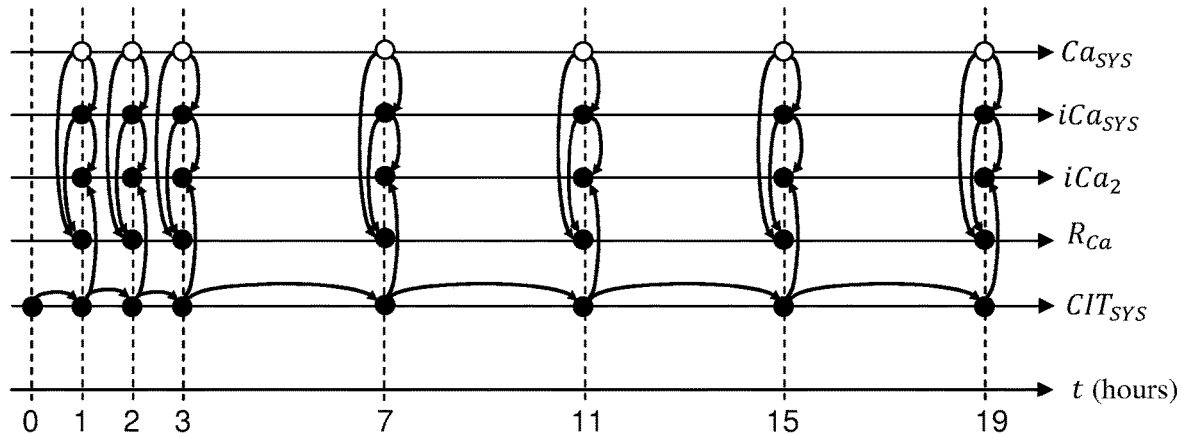
FIG. 8B $$iCa_2 = f_{0,1}(Ca_2, CIT_2) = \beta_0 + \beta_1 \cdot (Ca_2 - Ca_{REF}) + \beta_2 \cdot (CIT_2 - CIT_{REF})$$

$$Ca_2 = f_{0,2}(Ca_{SYS}, H, fpw, K_{Ca}, F_{CAL}, Q_B, Q_{PRE}, Q_E, Q_D, Q_{PBP})$$

$$CIT_2 = f_{0,3}(CIT_{SYS}, H, fpw, K_{CIT}, D_{CIT}, Q_B, Q_{PRE}, Q_E, Q_D, Q_{PBP})$$

$$CIT_{SYS} = f_{0,4}(CIT_0, V_D, K_{BODY}, G_{MET}, D_{CIT}, Q_B, K_{CIT}, t)$$

$$K_Y = f_{0,5}(k_0 A_Y, \alpha_Y, Q_B, Q_D, Q_{UF})$$

$$Ca_{SYS} = f_{0,6}(iCa_{SYS}, Alb, HCO_3, pH, EQ_{CaX}, iCIT, iCa_{REF}, iP)$$

$$iCa_{SYS} = f_{0,7}(Ca_{SYS}, Alb, HCO_3, pH, EQ_{CaX}, iCIT, iCa_{REF}, iP)$$

$$iCa_{SYS} = f_{0,7}^*(Ca_{SYS}, CIT_{SYS}) = \beta_{0\_2} + \beta_{1\_2} \cdot (Ca_{SYS} - Ca_{REF\_2}) + \beta_{2\_2} \cdot (CIT_{SYS} - CIT_{REF\_2})$$

FIG. 10

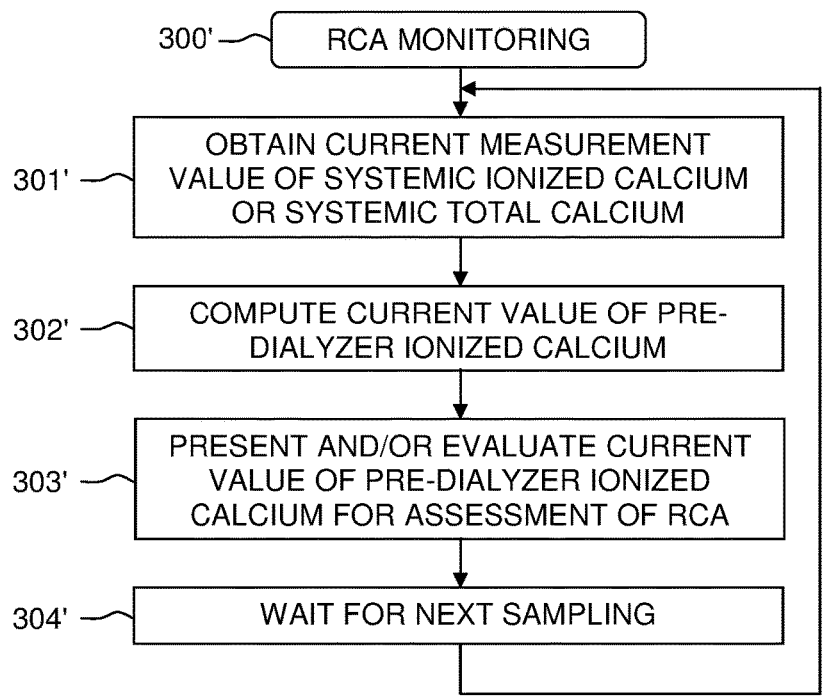

FIG. 11

PERFORMANCE MONITORING OF REGIONAL CITRATE ANTICOAGULATION

PRIORITY CLAIM

The present application is a National Phase of International Application No. PCT/EP2019/079721, filed Oct. 30, 2019, which claims priority to Swedish Application No. 1851551-0, filed Dec. 11, 2018. The entire contents of each application are incorporated herein by reference and relied upon.

TECHNICAL FIELD

The present invention relates to regional citrate anticoagulation (RCA) during blood treatment, and in particular to a technique for performance monitoring during a blood treatment that involves RCA, e.g. a continuous or semi-continuous renal replacement therapy.

BACKGROUND ART

Continuous or semi-continuous renal replacement therapies have become established as the treatment of choice for supporting critically ill patients with acute kidney injury. Continuous renal replacement therapy (CRRT) is typically a 24-hour treatment, whereas semi-continuous therapy may be performed daily with a duration of 6-12 hours or more. There are many different forms or "modalities" of continuous or semi-continuous renal replacement therapies, including but not limited to CVVH (continuous veno-venous hemofiltration), CVVHD (continuous veno-venous hemodialysis), CVVHDF (continuous veno-venous hemodiafiltration), SLEF (slow extended hemofiltration), SLED (sustained low-efficiency dialysis), and SCUF (slow continuous ultrafiltration). Common to these therapies is that they operate with a relatively low blood flow rate in the extracorporeal blood circuit, typically less than 200 ml/min. Renal replacement therapy involves passing the patient's blood through plastic tubings and membranes (e.g. in a dialyzer), which triggers clotting as well as complement cascade. Continuous and semi-continuous therapies usually require some degree of anticoagulation to prevent clotting in the extracorporeal blood circuit. Without anticoagulation, the survival of tubings and membranes is diminished and therapy becomes less effective.

Citrate or citric acid ($C_6H_8O_7$) is present in the human plasma, among other forms, as a trivalent negative citrate anion. This ion chelates ionized calcium ($Ca^{2+}$) in the plasma resulting in a single negative calcium-citrate complex and in low levels of free ionized calcium. Since the coagulation cascade requires free ionized calcium for optimal function, blood clotting in the extracorporeal blood circuit may be prevented by infusion of citrate into the withdrawal (arterial) limb of the extracorporeal blood circuit. As citrate is a small molecule, a majority of the calcium-citrate complex is moved across the membrane of the dialyzer and is lost in the dialysate effluent. To replace lost calcium, a local infusion of free ionized calcium is made into the return (venous) limb of the extracorporeal blood circuit or directly into the patient. Theoretically, this type of Regional Citrate Anticoagulation, commonly abbreviated RCA or CRA, is both very powerful and fully reversible without systemic (intra-patient) bleeding tendencies.

However, RCA has a potential for causing electrolyte abnormalities. Reported derangements by RCA include metabolic alkalosis and acidosis, hypernatremia and hyponatremia, and hypocalcemia. Such abnormalities are detected with proper monitoring and the local treatment protocol should describe how to adjust fluid flows under different conditions to counteract or prevent the abnormalities. The incidence of metabolic complications depends on the amount of citrate administered, the design, rules and flexibility of the protocol, and its proper use.

During RCA, it is common practice to measure the calcium blood status in two locations; a first location representing the blood in the patient and a second location with the highest risk of clotting. Depending on the local treatment protocol, the first location may be in the patient or at an upstream end of the extracorporeal blood circuit, resulting in "systemic" measurement values, and the second location may be upstream or downstream the dialyzer in the extracorporeal blood circuit, resulting in "pre-dialyzer" and "post-dialyzer" measurement values, respectively. The concentration of ionized calcium at the second location is monitored to ensure a low risk for coagulation in the extracorporeal blood circuit and may be used for modifying citrate dose accordingly. The level of systemic ionized calcium (at the first location) is monitored to ensure that the calcium infusion is capable of maintaining systemic ionized calcium levels within physiological range and may be used for modifying calcium infusion rate accordingly. For example, a target value for post-dialyzer ionized calcium may be in the range 0.3-0.5 mmol/L and a target value for systemic ionized calcium may be in the range 1.1-1.25 mmol/L.

One serious and potentially life-threatening complication of RCA is citrate accumulation in the patient. In clinical practice, the total-to-ionized calcium ratio (aka calcium ratio), which is related to the blood citrate concentration, is commonly accepted as an indirect index of citrate accumulation during RCA. For example, a calcium ratio $\geq 2.5$ may imply an increased risk of metabolic complications. To enable evaluation of the calcium ratio, the total calcium in the patient (aka total systemic calcium or systemic total calcium) is monitored together with the systemic ionized calcium.

Thus, protocols for RCA typically prescribe monitoring of at least three calcium values, namely ionized calcium at the first and second locations and total calcium at the first location, and often one or more additional systemic blood parameters, such as pH, bicarbonate, potassium, serum sodium, etc. Ionized calcium may be measured by sampling and subsequent sample analysis, e. g. by a blood gas analyzer, where the sampling and sample analysis may be performed every 20 minutes at startup of RCA and then at least every 6 hours when stable conditions are attained. Systemic total calcium may be measured by a laboratory test of a blood sample and may be performed at least once daily.

Further details regarding RCA and its implementations and complications are found in the articles "*Citrate anticoagulation for continuous renal replacement therapy (CRRT) inpatients with acute kidney injury admitted to the intensive care unit*", by Davenport and Tolwani, published in NDT Plus (2009) 2:439-447, and "*Complication of regional citrate anticoagulation: accumulation or overload?*", by Schneider et al., published in Critical Care (2017) 21:281.

RCA is known to be laborious, costly and complex, partly because of the need for frequent measurements of blood parameters, including ionized calcium. Further, conventional blood gas analyzers are typically not approved for typical concentrations of post-dialyzer ionized calcium (e.g. 0.2-0.5 mmol/L), nor for samples having high levels of citrate. Thus, it has been shown that the current practice of performing sampling and blood gas analysis may be afflicted by measurement errors, e.g. in the article "*Discrepant post filter ionized calcium concentrations by common blood gas analyzers in CRRT using regional citrate anticoagulation*" by Schwarzer et al., published in Critical Care (2015) 19:321.

There is a general need to improve the practice of using RCA during renal replacement therapy, with respect to at least one of simplicity, cost and accuracy.

The prior art comprises US2008/0015487 which proposes to install an online clearance monitor (OCM) for precise measurement of the delivered small solute clearance, and an online sensor system (OSS) for measuring free ionized levels of calcium, magnesium and citrate in the effluent fluid. It is further proposed to use the measurement values provided by the OSS to back-calculate the corresponding values in the patient's plasma. Allegedly, it is possible to mathematically derive the patient's plasma citrate and total calcium and magnesium level and thereby eliminate the need for laboratory monitoring of the patient's systemic total and ionized calcium and magnesium levels during RCA. However, the proposed use of an OCM and an OSS will not only add significant cost but also considerable complexity to the therapy, e.g. with respect to calibration and maintenance of the OCM and OSS.

WO2010/029401 presents a method for controlling, in continuous dialysis using RCA, the local infusion of calcium by calculations based on modeling of the reactions in the blood circulation, or by approximation of calcium clearance, in accordance with the actual flow rates and the mode of treatment. Specifically, it is proposed to control a pump for local infusion of a calcium solution as a function of the flow rate of blood entering the arterial line, the flow rate of effluent fluid from the dialyzer and the flow rate of citrate, while presuming a known concentration of the infused calcium solution and a fixed value of the systemic total calcium.

WO2010/148194 relates to conventional intermittent hemodialysis for patients suffering from chronic kidney disease (CKD) and proposes to perform RCA by combining infusion of citrate with the use of a dialysate containing both citrate and calcium, to thereby reduce or eliminate the need for post-dialyzer calcium infusion. A method is also proposed for blind prediction of the concentration of systemic ionized calcium at any point during the dialysis treatment or after completed dialysis treatment ("post-dialysis"), by use of a time-dependent mathematical model that includes processes in the patient affecting both calcium and citrate. The blind prediction implies that the systemic ionized calcium is blindly calculated as a function of time based solely on an initial measurement, e.g. at the start of dialysis treatment. There is no indication about the parameters that are measured in the initial measurement. The blind prediction involves computation of predicted concentrations of citrate and ionized calcium at various locations in the extracorporeal blood circuit. Since the mathematical model represents processes in the patient affecting calcium, it is further proposed to statistically correct the predicted concentration of post-dialysis systemic ionized calcium by accounting for the patient's parathyroid hormone (PTH) and/or alkaline phosphatase (AP) level. The correction is determined by employing a multivariate linear regression model including a category of the PTH or AP level of the patient, dialysis treatment time and the predicted concentration of post-dialysis systemic ionized calcium. A corresponding disclosure is found in the article "*A Mathematical Model of Regional Citrate Anticoagulation in Hemodialysis*", by Thijssen et al., published in Blood Purif 2010; 29:197-203.

SUMMARY

It is an objective of the invention to at least partly overcome one or more limitations of the prior art.

A further objective is to improve the practice of using RCA during renal replacement therapy, with respect to at least one of simplicity, cost and accuracy.

One or more of these objectives, as well as further objectives that may appear from the description below, are at least partly achieved by a monitoring device, a blood treatment system, a method of monitoring, and a computer-readable medium, embodiments thereof being defined by the dependent claims.

A first aspect of the invention is a monitoring device for a blood treatment system. The blood treatment system comprises an extracorporeal blood circuit which comprises a blood withdrawal line and a blood return line for connection to a vascular system of subject and a dialyzer intermediate the blood withdrawal and blood return lines. The blood treatment system is configured for regional citrate anticoagulation, RCA, by administration of citrate to the extracorporeal blood circuit upstream of the dialyzer during a treatment session. The monitoring device is configured to, at consecutive time steps during the treatment session: obtain a current measurement value of systemic ionized calcium or systemic total calcium; operate a predefined algorithm on the current measurement value to generate a current computation value that represents ionized calcium in blood at a selected location downstream or upstream of the dialyzer in the extracorporeal blood circuit; and present and/or evaluate the current computation value for assessment of the regional citrate anticoagulation.

The first aspect makes it possible to dispense with or at least significantly reduce the need for the conventional procedure of taking and analyzing blood samples upstream and/or downstream of the dialyzer in the extracorporeal blood circuit. Instead, by the first aspect, corresponding information is obtained by algorithmic computations based on a measurement value of systemic ionized calcium or systemic total calcium. Such a measurement value may be obtained in accordance with conventional practice. Thus, the first aspect may serve to reduce the number blood samples that need to be taken and analyzed for monitoring the performance of the regional citrate anticoagulation. The complexity of performing blood treatment in combination with RCA is thereby reduced. Further, lowering the number of blood samples will free time for clinical staff as well as save expenditure for blood sample analysis. Although it may seem counter-intuitive, the accuracy of the computation value, at least when representing post-dialyzer ionized calcium, may even be better than the accuracy of the corresponding measurement value obtained by the conventional approach of performing blood sampling and subsequent blood sample analysis. As noted above, conventional blood gas analyzers are not optimized for blood that is sampled downstream of the dialyzer in the extracorporeal blood circuit and the resulting measurement value lacks in both accuracy and precision. On the other hand, there are established procedures and devices for measuring ionized and total calcium in the blood of the patient, i.e. systemic values, with high accuracy. Thus, by starting from a relatively accurate measurement value of systemic ionized calcium or systemic total calcium, it is not unlikely that the computation value produced by the first aspect is more accurate than the conventionally measured value.

The ability of the first aspect to provide a sufficient accuracy is also due to the fact that the current computation value is generated by operating the predefined algorithm on a current measurement value of systemic ionized calcium or systemic total calcium, e.g. a measurement value that is obtained anew to be relevant at the respective time step. Thereby, the computation starts from the actual level of ionized or total calcium in the subject's blood at each time step. Compared to using predicted levels of calcium in the extracorporeal blood circuit or the subject, the use of actual levels is more likely to render accurate results.

In the following, various embodiments of the first aspect are defined. These embodiments provide at least some of the technical effects and advantages described in the foregoing, as well as additional technical effects and advantages as readily understood by the skilled person, e.g. in view of the following detailed description.

In one embodiment, the monitoring device is further configured to obtain input data comprising current values of operation parameters of the blood treatment system, and optionally one or more of system configuration data for the blood treatment system, chemical parameter data for substances in the blood, and physiological parameter data for the subject, and the monitoring device is configured to operate the predefined algorithm on the input data and the current computation value to generate the current computation value.

In one embodiment, the predefined algorithm comprises a first function configured to estimate the ionized calcium in the blood at the selected location in the extracorporeal blood circuit, said first function being linearly dependent on total calcium at the selected location and total citrate at the selected location.

In one embodiment, the first function is obtained by linearization of a non-linear function with respect to each of total calcium and total citrate, wherein the non-linear function is a solution to a system of equations representing chemical reactions of calcium in free form and bound to other substances in blood, including citrate, while assuming predefined amounts of other substances than calcium and citrate.

In one embodiment, the linearization is performed with respect to reference values of total calcium and total citrate, said reference values corresponding to expected values of total calcium and total citrate, respectively, at the selected location.

In one embodiment, the predefined algorithm comprises a second function configured to estimate the total calcium in the blood at the selected location.

In one embodiment, the selected location is downstream of the dialyzer, and the second function depends on the systemic total calcium and represents a mass balance of total calcium that enters the extracorporeal blood circuit in the blood from the subject and total calcium in the blood at an intermediate location in the extracorporeal blood circuit upstream of the dialyzer, while accounting for fluid infusion into the extracorporeal blood circuit intermediate the subject and the intermediate location, wherein the second function further accounts for a loss of total calcium from the blood in the dialyzer.

In one embodiment, the predefined algorithm comprises a third function configured to estimate the total citrate in the blood at the selected location in the extracorporeal blood circuit.

In one embodiment, the selected location is downstream of the dialyzer, and the third function depends on systemic total citrate and represents a mass balance of total citrate that enters the extracorporeal blood circuit in the blood from the subject and total citrate at an intermediate location in the extracorporeal blood circuit upstream of the dialyzer, while accounting for fluid infusion into the extracorporeal blood circuit intermediate the subject and the intermediate location, wherein the third function further accounts for a loss of total citrate from the blood in the dialyzer.

In one embodiment, the predefined algorithm further comprises a fourth function configured to estimate systemic total citrate as a function of time from start of the regional citrate anticoagulation.

In one embodiment, the fourth function represents a metabolic generation rate of citrate in the subject and further accounts for the administration of citrate into the extracorporeal blood circuit upstream of the dialyzer and a loss of total citrate from the blood in the dialyzer.

In one embodiment, the predefined algorithm further comprises at least one fifth function configured to estimate a clearance of total citrate and a clearance of total calcium from the blood in the dialyzer, wherein the monitoring device is configured to compute a loss of total citrate and a loss of total calcium in the dialyzer based on the clearance of total citrate and the clearance of total calcium, respectively.

In one embodiment, the predefined algorithm comprises a sixth function configured to estimate systemic total calcium as a function of the systemic ionized calcium.

In one embodiment, the predefined algorithm comprises a seventh function configured to estimate the systemic ionized calcium as a function of the systemic total calcium.

In one embodiment, the current measurement value represents the systemic ionized calcium in the blood of the subject, and the monitoring device is further configured to operate the predefined algorithm on the current measurement value to generate a further current computation value representing the systemic total calcium.

In an alternative embodiment, the current measurement value represents the systemic total calcium, and the monitoring device is further configured to operate the predefined algorithm on the current measurement value to generate a further current computation value representing the systemic ionized calcium.

In one embodiment, the monitoring device is further configured to operate the predefined algorithm to generate a further current computation value representing systemic total citrate.

In one embodiment, the monitoring device is further configured to evaluate at least the further current computation value for assessment of accumulation of citrate in the subject.

In one embodiment, the monitoring further comprises an interface for signal communication with a blood analysis apparatus, wherein the monitoring device is further configured to, at the respective consecutive time step, obtain the measurement value from a signal received over the interface from the blood analysis apparatus.

In one embodiment, the monitoring device is further configured to output the current computation value for presentation on a display device.

In one embodiment, the monitoring device is further configured to evaluate the current computation value for detection of an alarm situation, and cause an alarm to be generated when the alarm situation is detected.

In one embodiment, the monitoring device further comprises a decision support module, which is configured to evaluate the current computation value in relation to a clinically proven protocol for the regional citrate anticoagulation, obtain a recommendation for operation of the blood treatment system based on the protocol, and output the recommendation for presentation on a display device.

In one embodiment, the monitoring device further comprises an interface for signal communication with a set of pumping devices in the blood treatment system, wherein the monitoring device is further configured to generate one or more control signals for the set of pumping devices as a function of the current computation value, and provide the one of more control signals to the interface.

In one embodiment, the monitoring device is further configured, during the treatment session, to obtain measurement data representing at least one of calcium and citrate in the blood of the subject and/or the extracorporeal blood circuit, and adjust the predefined algorithm based on the measurement data.

A second aspect is a blood treatment system comprising an extracorporeal blood circuit for connection to a vascular system of a subject. The extracorporeal blood circuit comprises a blood withdrawal line and a blood return line for connection to the vascular system, and a dialyzer intermediate the blood withdrawal and blood return lines. The blood treatment system further comprises a pumping device for pumping blood from the subject through the blood withdrawal line, the dialyzer and the blood return line back to the subject. The blood treatment system further comprises a sub-system which is operable to perform regional citrate anticoagulation, RCA, in relation to the extracorporeal blood circuit and the subject, and a monitoring device in accordance the first aspect or any of its embodiments.

A third aspect of the invention is a method of monitoring a blood treatment system comprising an extracorporeal blood circuit which is configured for connection to a vascular system of a subject and comprises a dialyzer, wherein the blood treatment system is configured for regional citrate anticoagulation, RCA, by administration of citrate to the extracorporeal blood circuit upstream of the dialyzer during a treatment session. The method comprises, at consecutive time steps during the treatment session: obtaining a current measurement value of systemic ionized calcium or systemic total calcium; operating a predefined algorithm on the current measurement value to generate a current computation value representing ionized calcium in blood at a selected location downstream or upstream of the dialyzer in the extracorporeal blood circuit; and presenting and/or evaluating the current computation value for assessment of the regional citrate anticoagulation.

Any one of the embodiments of the first aspect may be adapted and implemented as an embodiment of the third aspect.

A fourth aspect of the invention is a computer-readable medium comprising computer instructions which, when executed by a processor, cause the processor to perform the method of the third aspect and any of its embodiments.

Still other objectives, features, embodiments, aspects and advantages of the present invention may appear from the following detailed description, from the attached claims as well as from the drawings.

BRIEF DESCRIPTION OF THE DRAWINGS

Embodiments of the invention will now be described in more detail with reference to the accompanying drawings.

FIG. 6 is a table of machine settings, physiological parameters, system parameters and chemical parameters for use in computations by the system in FIG. 4.

FIGS. 8A-8B show calculations of RCA-related parameters at a series of time steps based on concurrent measurements of systemic ionized calcium and systemic total calcium, respectively.

FIG. 10 is an overview of functions that may be included in a predefined algorithm for use in RCA monitoring.

FIG. 11 is a flow chart of an alternative method of RCA monitoring.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Embodiments of the invention are applicable to all forms of extracorporeal blood treatment or processing that may be combined with regional citrate anticoagulation (RCA), including acute dialysis therapies such as the continuous or semi-continuous renal replacement therapies discussed in the Background section, as well as chronic dialysis therapies such as intermittent hemodialysis, hemofiltration, hemodiafiltration and ultrafiltration etc, and hybrid dialysis therapies such as prolonged intermittent renal replacement therapy (PIRRT), sustained low-efficiency dialysis (SLED), and extended daily dialysis (EDD) etc. Conventionally, the different types of dialysis therapy are referred to as "modalities".

In the following, without limitation, embodiments will be described with reference to Continuous Renal Replacement Therapy (CRRT) and modalities thereof.

Figure 1:
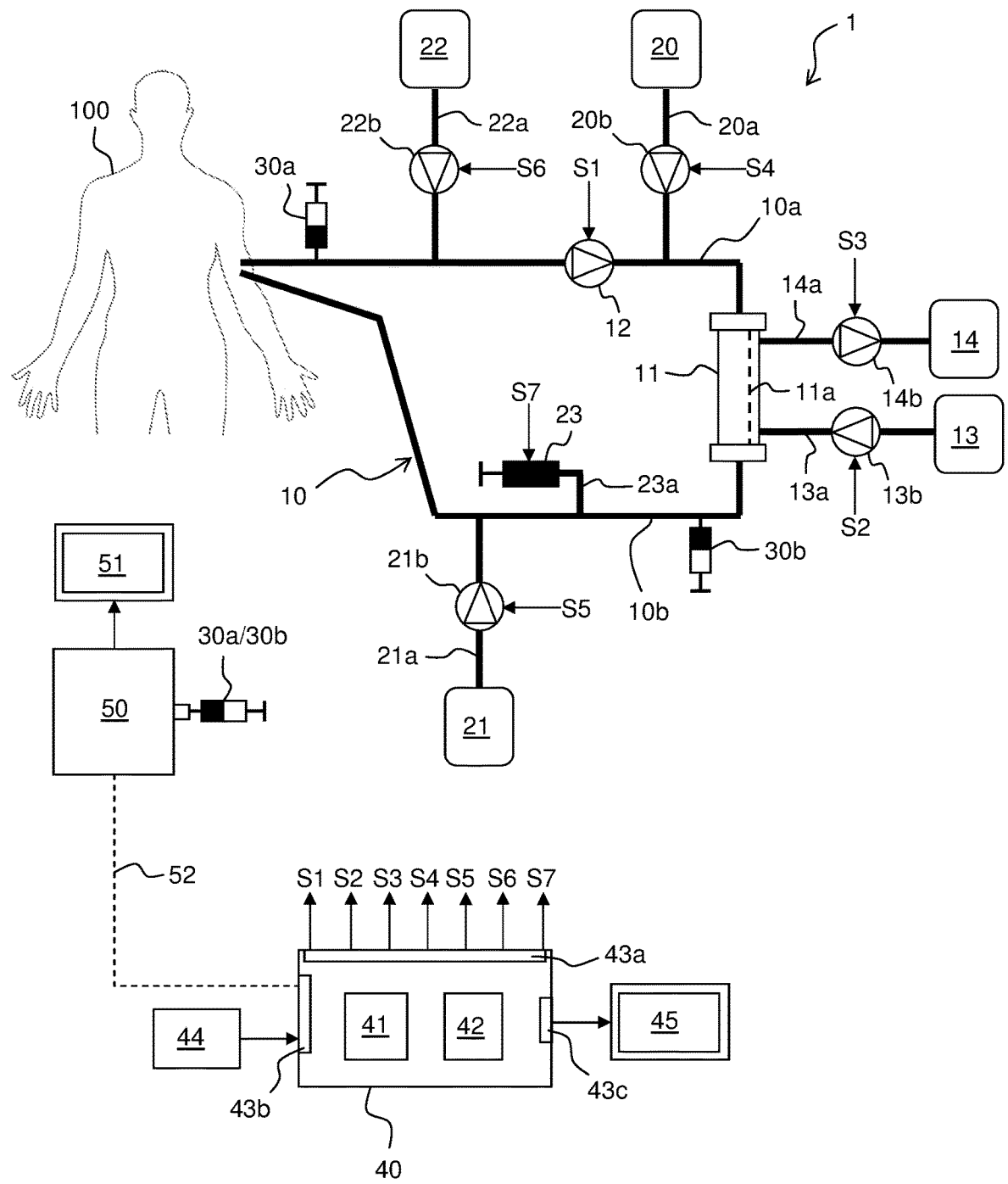
FIG. 1 is a schematic overview of a CRRT system configured for use with RCA.

FIG. 1 is a schematic view of a blood treatment system 1 for performing CRRT in combination with RCA when connected to a human subject 100, denoted "patient" in the following. The system 1 comprises an extracorporeal blood circuit ("EC circuit") 10 which is connected to the vascular system of the patient 100 at a blood withdrawal end and a blood return end. The connections may be performed by any conventional device, such as a needle or catheter. Blood lines or tubings are arranged to define a blood withdrawal path or limb 10a and a blood return path or limb 10b of the EC circuit 10. A blood filtration unit 11, denoted "dialyzer" herein, is connected between the withdrawal and return paths 10a, 10b. The dialyzer 11 comprises a semi-permeable membrane 11a, which is arranged to separate the dialyzer 11 into a blood compartment, which is fluidly connected to the withdrawal and return paths 10a, 10b, and a dialysis fluid compartment. A blood pump 12 is arranged in the withdrawal path 10a and is operable to draw blood from the patient 100 and pump the blood via the blood compartment of the dialyzer 11 and through the return path 10b back to the patient 100. The system 1 further comprises a source 13 of dialysis fluid. A dialysis fluid path or line 13a connects the source 13 to the dialysis fluid compartment of the dialyzer 11. Similarly, an effluent path or line 14a connects the dialysis fluid compartment of the dialyzer 11 to a sink 14 for spent dialysis fluid (denoted "effluent" in the following). A dialysis fluid pump 13b is arranged in the dialysis fluid path 13a, and an effluent pump 14b is arranged in the effluent path 14a.

In the illustrated example, the system 1 further comprises a first source 20 of replacement fluid which is connected by a first replacement fluid line 20a to the withdrawal path 10a intermediate the blood pump 12 and the dialyzer 11. A first replacement fluid pump 20b is arranged in the first replacement fluid line 20a. The system 1 further comprises a second source 21 of replacement fluid which is connected by a second replacement fluid line 21a to the return path 11a. A second replacement fluid pump 21b is arranged in the second replacement fluid line 21a.

The system 1 further comprises an arrangement for pre-dialyzer infusion of citrate into the EC circuit 10. The citrate infusion arrangement includes a source 22 of a citrate-containing fluid. A citrate fluid line 22a connects the source 22 to the withdrawal path 10a upstream of the blood pump 12. A citrate pump 22b is arranged in the citrate fluid line 22a.

The system 1 further comprises an arrangement for post-dialyzer infusion of ionized calcium into the EC circuit 10. The calcium infusion arrangement includes a source 23 of a calcium-containing fluid. In the illustrated example, a calcium fluid line 23a connects the source 23 to the return path 10b intermediate the dialyzer 11 and the second replacement fluid line 21a. In other examples, the line 23a may be connected to the return path 10b downstream of the second replacement fluid line 21a, or directly to the vascular system of the patient 100. In the illustrated example, the source 23 is a syringe pump which is operable to infuse the calcium-containing fluid. In an alternative, a separate calcium pump is arranged in the calcium fluid line 23a downstream of the source 23.

The system 1 is operated by a control device 40, which is configured to generate control signals S1-S7 for the pumps 12, 13b, 14b, 20b, 21b, 22b and 23 at least partly in accordance with a control program comprising computer instructions. The control program may also operate based on measurement signals received by the control device 40 from sensors (not shown) in the system 1. The control device 40 comprises a processor 41 and computer memory 42. The control program is stored in the memory 42 and executed by the processor 41. The control program may be supplied to the control device 40 on a computer-readable medium, which may be a tangible (non-transitory) product (e.g. magnetic medium, optical disk, read-only memory, flash memory, etc) or a propagating signal. In the illustrated example, the control device 40 comprises a control signal interface 43a for providing the control signals S1-S7 to the pumps in the system 1. The control device 40 also comprises an input interface 43b for connection to one or more input devices 44 that enables an operator to input control data, as well as an output interface 43c for connection to one or more output devices 45 for providing feedback data to the operator. For example, the input device(s) 44 may comprise a keyboard, keypad, computer mouse, control button, touch screen, printer, etc, and the output device(s) 45, may comprises a display device, an indicator lamp, an alarm device, etc. The operator may be a clinically experienced person, such as a physician or a nurse.

The control device 40 is operable to effect blood treatment in the system 1 by operating, in accordance with the control program, the pump 12 to circulate blood through the EC circuit 10, the pump 13b to supply dialysis fluid to the dialyzer 11, the pump 14b to remove effluent from the dialyzer 11, and the pumps 20a, 20b to infuse replacement fluid before the dialyzer 11 ("pre-infusion") and after the dialyzer 11 ("post-infusion"). The control device 40 is also operable to effect RCA in the system 1 by operating, in accordance with the control program, the pump 22b to infuse the citrate-containing fluid and the pump 23 to infuse the calcium-containing fluid. The underlying rationale for RCA and the infusion of citrate and calcium is described in the Background section and is also well-known to the person skilled in the art and will not be repeated here.

Although the system 1 in FIG. 1 is described for a modality that involves both dialysis, pre-infusion and post-infusion of replacement fluid, the system 1 may be modified into other modalities, e.g. by refraining from either of pre-infusion and post-infusion of replacement fluid, or both, and/or by performing pure ultrafiltration in the dialyzer 11 instead of dialysis. Further, embodiments of the invention are applicable to any clinically proven composition of the dialysis fluid, the replacement fluid, the citrate-containing fluid and the calcium-containing fluid, respectively.

FIG. 1 also indicates a conventional configuration of the system 1 for obtaining blood samples. As described in the Background section, in accordance with certain protocols, blood samples may be routinely taken to measure the level of systemic total calcium and systemic ionized calcium, as well as post-dialyzer ionized calcium. As used herein, "systemic" refers to the blood in the patient 100 and "ionized calcium" refers to the free calcium ions, $Ca^{2+}$. Further, the term "level" may be any type of relative or absolute measure, such as a concentration or an amount. In one non-limiting example, the post-dialyzer ionized calcium may be measured to monitor proper performance of anticoagulation, systemic ionized calcium may be measured to monitor proper performance of the calcium infusion, and the systemic total calcium may be monitored to evaluate citrate accumulation in the patient 100. The systemic ionized calcium and post-dialyzer ionized calcium are conventionally measured in blood samples that are taken by connecting a respective sampling device 30a, 30b to the EC circuit 10 at a respective designated location. Specifically, systemic ionized calcium is measured at the upstream end of the withdrawal path 10a, i.e. close to the connection to the patient 100 where fresh blood enters the EC circuit 10. Post-dialyzer ionized calcium is measured in the return path 10b, downstream of the dialyzer 11 and upstream of the calcium infusion. When the sampling device 30a, 30b has been operated to obtain a blood sample, the sampling device 30a, 30b is disconnected from the EC circuit 10 and connected to a blood analysis apparatus 50, which is separate from the system 1 and configured to analyze the blood sample for determination of the level of ionized calcium, and possibly other blood parameters such as level of pH, bicarbonate, magnesium, sodium, potassium, chloride, hematocrit, oxygenation, etc. Any suitable blood analysis apparatus 50 may be used, e.g. a so-called blood gas analyzer (BGA).

Alternatively, the systemic ionized calcium may be measured by BGA analysis of a blood sample which is taken from the patient.

The systemic total calcium is conventionally measured by laboratory analysis of a blood sample which is taken from the patient or at a location in the EC circuit 10 close to the connection to the patient 100, e.g. by use of the sampling device 30a. The apparatus 50 may present the result of the analysis of the respective blood sample to the operator on a display device 51, whereupon the operator may evaluate the measurement values based on clinical experience and practice to decide if any setting needs to be changed. If so, the operator may change the setting(s) via the input device 44. Alternatively, as indicated by a dashed line in FIG. 1, the blood analysis apparatus 50 may be connected to transfer the measurement values over a wired or wireless connection 52 to the control device 40 via its input interface 43b, whereby the control device 40 may show the measurement values to the operator on the display 45.

Figure 2:
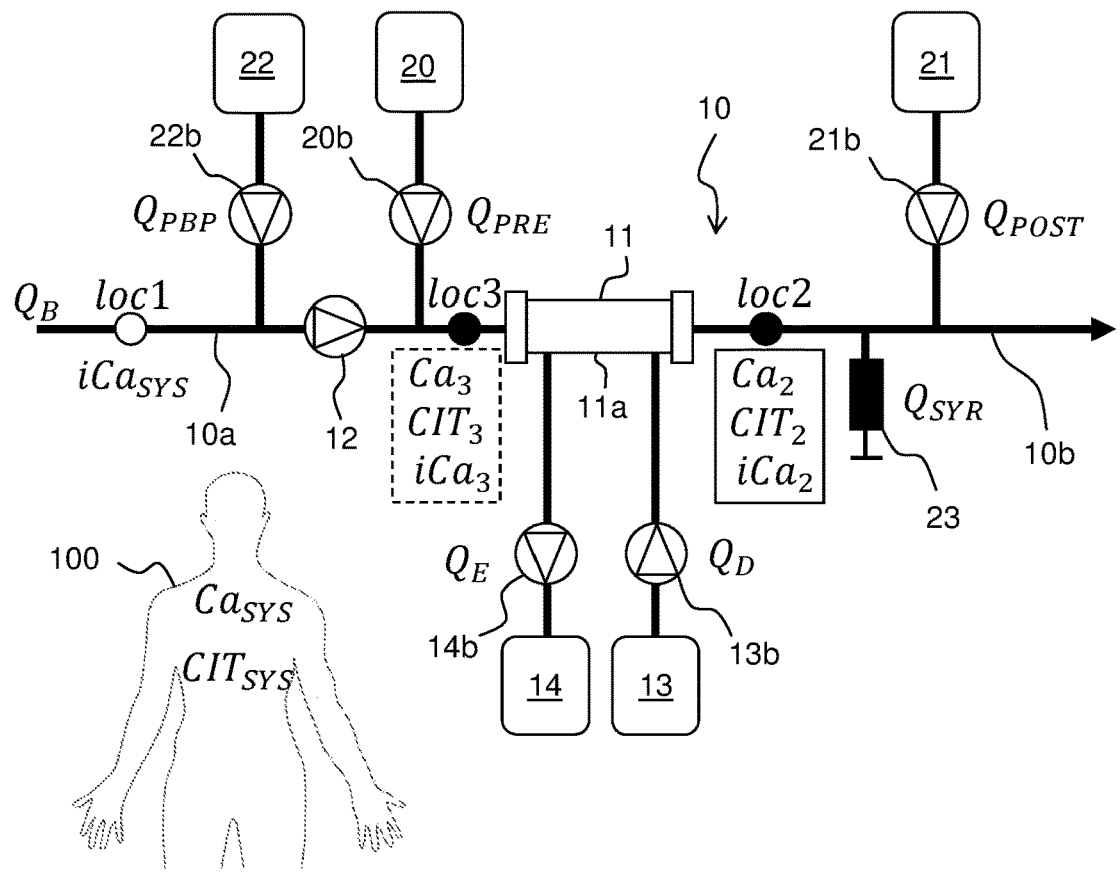
FIG. 2 corresponds to FIG. 1 and indicates machine parameters and locations for measurement and computation of calcium-related parameters during RCA monitoring.

FIG. 2 corresponds to FIG. 1 and shows the EC circuit 10 in linear outline, with blood from the patient entering at the left end and treated blood leaving at the right end. FIG. 2 also indicates parameters that may be used in computations in accordance with embodiments of the invention. The level of total calcium in the patient 100 is designated $Ca_{SYS}$ ("systemic total calcium"), and the level of total citrate in the patient 100 is designated $CIT_{SYS}$ ("total systemic citrate" or "systemic total citrate"). A first location at the upstream end of the EC circuit 10 is designated loc1 and the level of ionized calcium at loc1 is designated $iCa_{SYS}$ ("systemic ionized calcium"). A second location downstream of the dialyzer 11 is designated loc2 and the level of ionized calcium at loc2 is designated $iCa_2$ ("post-dialyzer ionized calcium"). Further, the level of total citrate and total calcium at loc2 is designated $CIT_2$ ("post-dialyzer total citrate") and $Ca_2$ ("post-dialyzer total calcium"), respectively. A third location upstream of the dialyzer 11 and downstream of the citrate administration and the pre-infusion (if present) is designated loc3. It should be realized that loc1 and loc2 correspond to the sampling locations in FIG. 1. The flow rate of blood taken from the patient is designated by $Q_B$. Further, the flow rates of pumps in the system is designated by $Q_D$ for the dialysis fluid pump 13b, $Q_E$ for the effluent pump 14b, $Q_{PRE}$ for the first replacement fluid pump 20b, $Q_{POST}$ for the second replacement fluid pump 21b, $Q_{PBP}$ for the citrate pump 22b, and $Q_{SYR}$ for the calcium pump 23.

If the total or ionized calcium is measured at loc1, the measured values may differ slightly from the actual values in the patient, e.g. as a result of so-called access recirculation at the connection site where the arterial path 10a is connected to the vascular system. To compensate for the difference, a correction factor may be empirically or theoretically determined and applied to the measured values.

By insightful reasoning and thorough simulation and experimentation, the inventors have found that it is possible to replace at least the measurement of post-dialyzer ionized calcium, $iCa_2$, by a computation of a corresponding parameter value based on a measurement value of either systemic total calcium, $Ca_{SYS}$, or systemic ionized calcium, $iCa_{SYS}$. Embodiments of the invention are based on this insight. The computation of $iCa_2$ will greatly reduce both cost and complexity of performing blood treatment in combination with RCA, since it obviates or at least reduces the need to regularly take blood samples downstream of the dialyzer 11 during blood treatment. As a conservative estimate, it takes at least 5 minutes for clinical staff to manually take the blood sample, transport the sampling device (30b in FIG. 1) to the blood analysis apparatus 50 and wait for the blood analysis. Assuming that 6-10 such samples are taken each day for each blood treatment machine, this corresponds to 30-50 minutes of qualified staff time. Further, the analysis of blood samples by the apparatus 50 also comes with an operational cost. Thus, for a clinic that operates a plurality of machines that perform blood treatment combined with RCA, considerable savings in both time and operational cost are enabled by embodiments of the invention.

Figure 3:
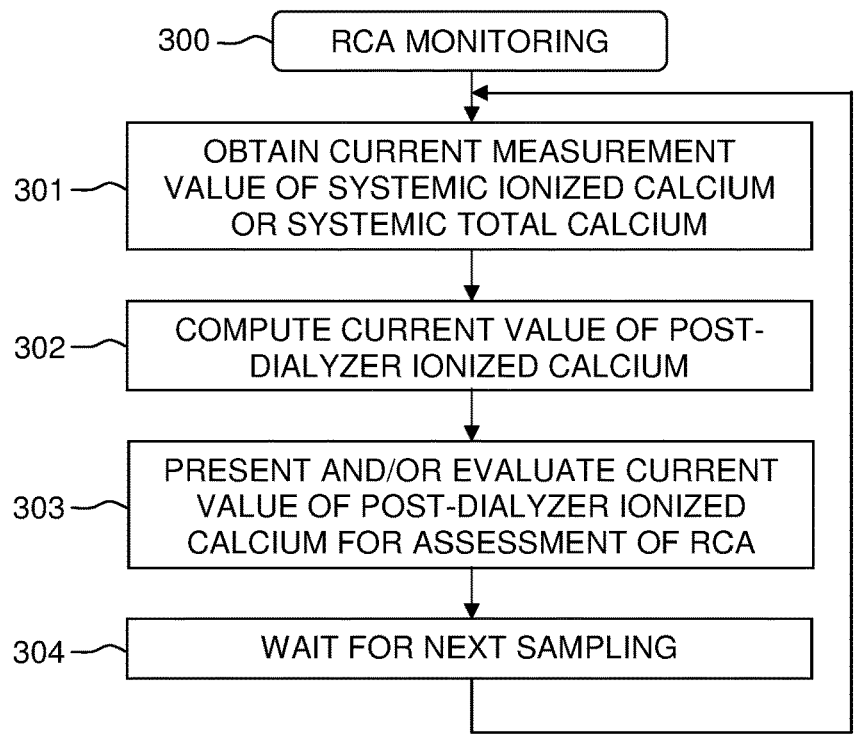
FIG. 3 is a flow chart of an example method of RCA monitoring.

FIG. 3 is a flow chart of a method 300 for performance monitoring of RCA during a blood treatment session in accordance with an embodiment. As used herein, a "blood treatment session" involves pumping blood through the EC circuit 11 when the latter has been arranged in fluid communication with the vascular system of the patient 100. The method 300 may be performed by the control program in the control device 40 (FIG. 1). Alternatively, the device 40 may be a dedicated monitoring device, whereas the control signals S1-S7 may be generated by a separate control device (not shown). In step 301, a current measurement value of systemic ionized calcium, $iCa_{SYS}$, or systemic total calcium, $Ca_{SYS}$, is obtained. With reference to the device 40 in FIG. 1, a current measurement value of $iCa_{SYS}$ may be obtained either by electronic transfer from the blood analysis apparatus 50 over communication line 52 or by the operator manually entering the measurement value through use of the input device 44. A current measurement value of $Ca_{SYS}$, which conventionally is given by a laboratory test, may be entered manually by the operator through use of the input device 44. In step 302, a current value of the post-dialyzer ionized calcium at loc2, i.e. $iCa_2$ (FIG. 2), is computed as a function of the current measurement value. Step 302 may involve operating a predefined algorithm on the current measurement value. It may be noted that step 301 may involve obtaining current measurement values of both iCa- $_{SYS}$ and $Ca_{SYS}$, and that step 302 may involve computing the current value of $iCa_2$ as a function of these current measurement values.

In step 303, the current value of $iCa_2$ is presented and/or evaluated for assessment of the RCA performance. For example, step 303 may involve presenting the current value of $iCa_2$ on a display device (cf. 45 in FIG. 1) or otherwise, to allow the operator to assess the RCA performance and take corrective action if deemed necessary. Alternatively or additionally, step 303 may involve a machine-implemented evaluation of the current value of $iCa_2$ for assessment of the RCA performance, which may result in, e.g., an alarm signal or a recommendation to the operator to change one or more settings of the system 1. Further examples of step 303 are given below with reference to FIG. 4. The method 300 then proceeds to step 304, in which it waits before returning to step 301. For example, step 304 may wait for a predefined time period, e.g. in accordance with a predefined sampling scheme as exemplified in the Background section. Alternatively, step 304 may proceed to step 301 whenever a new current measurement value of $iCa_{SYS}$ or $Ca_{SYS}$ is received by method 300.

From the flow chart in FIG. 3, it is seen that the computation of the current value of $iCa_2$ is based on a measurement value which is obtained anew for each repetition of steps 301-303. Thus, the computation of the current value of $iCa_2$ does not require the level of ionized or total calcium in the patient or in the EC circuit 10 to be projected over time. The skilled person realizes that the accuracy of the computed value is likely to increase when it is based on actual measurements rather than projections.

Figure 4:
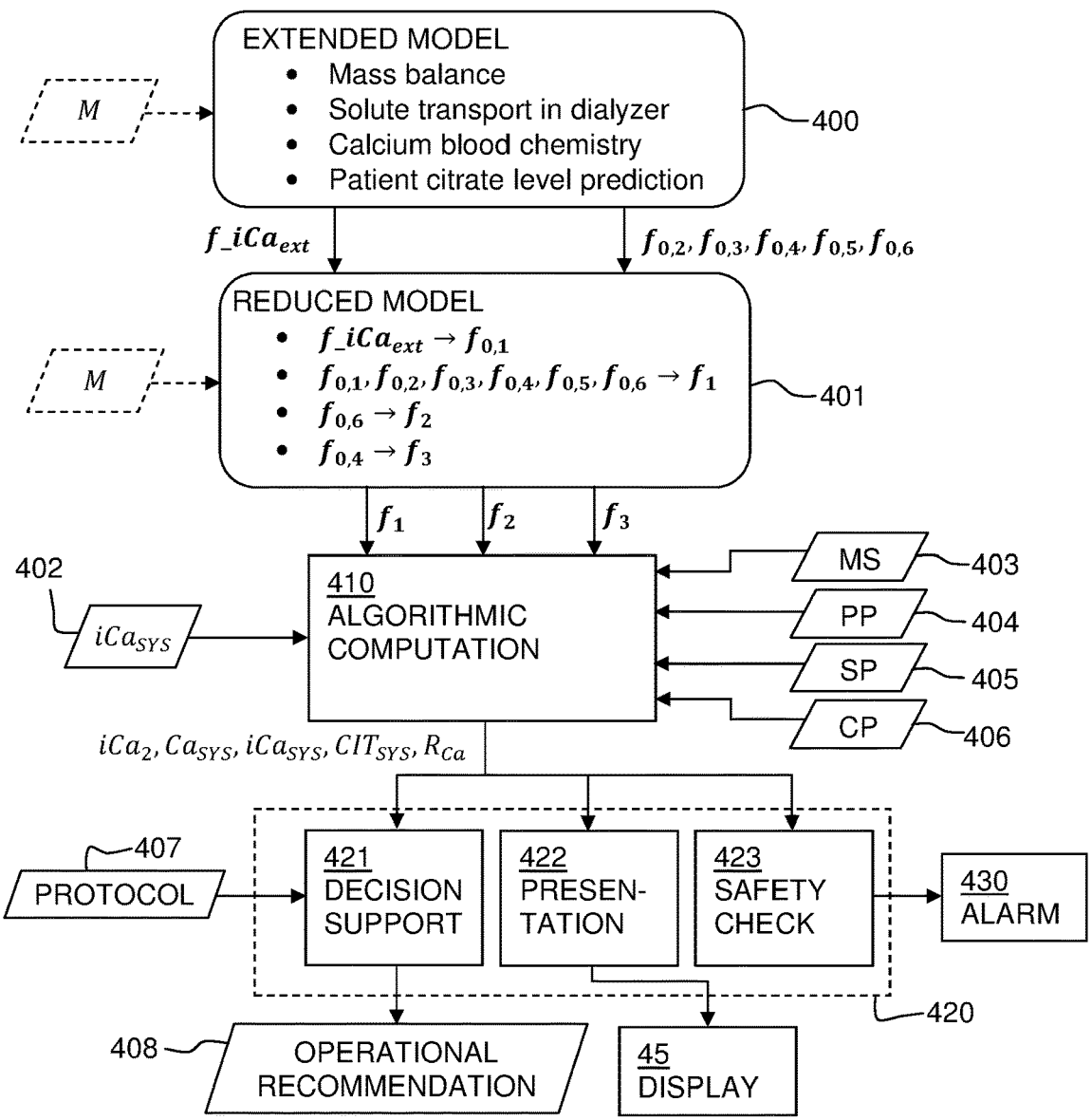
FIG. 4 is a block diagram of an example system for RCA monitoring.

FIG. 4 is a block diagram of a system for RCA monitoring in accordance with an embodiment. Blocks 400-401 represent preparatory modeling and analysis for determining the predefined algorithm to be used in the RCA monitoring. Blocks 402-407 represent input data, and block 408 represents output data. Blocks 410 and 421-423 represent functional modules or processes that may be implemented in a monitoring device (cf. 40 in FIG. 1). In the following description of FIG. 4, reference is made to parameters that are defined in the nomenclature list at the end of the detailed description.

Block 400 involves defining an extended model of the system 1 and the patient 100 for the purpose of deriving an algorithm that defines the level of post-dialyzer ionized calcium. Such an extended model comprises a model of the relevant blood chemistry, including the interactions of calcium with other substances in the blood. The interactions are defined by a number of chemical reactions. The outcome of these reactions is determined by the local concentration of the reactants and chemical equilibrium constants together with the total amounts of calcium and other substances. The total of a substance is the sum of all its forms. The total concentrations depend on the composition of the blood that is pumped from the patient 100, the fluids that are mixed into the EC circuit 10, and the transport of substances over the membrane 11a. The blood chemistry includes calcium, both in free form and bound to other substances. In one example, the model of blood chemistry includes calcium in free form and calcium binding to citrate, albumin, bicarbonate, phosphate and carbonate, as well as substances that are competing to bind to citrate, albumin, bicarbonate, phosphate and carbonate, such as magnesium, sodium, and hydrogen. In embodiments of the invention, the concentration of calcium in the patient 100 is measured as total concentration ($Ca_{SYS}$) or as ionized (free) concentration ($iCa_{SYS}$). In one example, the model of blood chemistry assumes that the amount/concentration of the modeled substances other than calcium and citrate are known (e.g. measured or estimated) with the exception of citrate which is modeled over treatment time based on the known addition of citrate for anticoagulation (by pump 22b in FIG. 2). For example, the modeled substances other than calcium and citrate may be assumed to be constant over time.

In one example, the extended model quantifies each included reaction by its equilibrium constant (EQ), giving the equation: $([AB])/([A] \cdot [B]) = EQ$, where the complex AB is formed by A and B, and [ ] denotes concentration.

The extended model accounts for the addition of fluids into the EC circuit 10 by considering the mass balance of each substance. Thus, the concentration of substance at loc3 (FIG. 2) is given by the mass flow of the substance at loc1 and considering any mass flow of the substance into the EC circuit 10 upstream of loc3.

The concentration of post-filter total calcium is dependent on the amount of the total calcium that is free for transport over the membrane 11a and the amount of protein-bound calcium that cannot pass the membrane 11a. When using RCA, a relatively large portion of free calcium will bind citrate, and citrate-calcium complexes will be lost through the membrane 11a. In one example, the extended model involves computing the clearance for different solutes in the dialyzer 11 as a function of the flow rates and the concentrations of the solute at the inlets of the dialyzer. The term "clearance" is well-known to the skilled person and is defined as the mass transfer rate for a solute divided by its plasma concentration or by the concentration gradient if the solute is present on both sides of the membrane 11a. In the present disclosure, no distinction is made between clearance and dialysance. The clearance depends on the flow rates of blood and dialysis fluid, the applied ultrafiltration rate ($Q_{FIL}$), and characteristics of the membrane 11a. There are established equations for computing clearance for small uncharged water soluble substances, both under pure diffusive conditions and with significant convective transport across the membrane 11a. In one example, the extended model may be based on the principles disclosed in the article "*Diffusive-convective mass transfer rates for solutes present on both sides of a dialyzer membrane*" by Sternby et al, published in ASAIO J 51(3):246-251, 2005. The equations in the article are given for uncharged substances, and thus the mass transport rate is assumed to be a linear function of the inlet concentrations, since the driving forces for diffusion and convection are linear. For charged solutions, equations for clearance may also consider the electrical potential across the membrane. If required, such a membrane potential arises to maintain electro-neutrality. Since all of the charged solutes act together, a calculation of the transportation of one ion may, to be reasonably accurate, consider other relevant ions in the solution. Further, calculation of solute transportation may also consider complex binding between ions. When a complex transfers across the membrane 11a, its concentration will change on both sides of the membrane 11a and affect the equilibrium between the complex and its individual components. Since, these changes affect the concentration gradient and the transport rate for these components across the membrane 11a, equilibrium equations may be included in the calculation of the mass transfers. The calculation of mass transfer rates involves the mass transfer area coefficients of the various solutes, which are available in handbooks or may be estimated. In one example, the extended model considers complexes formed with albumin, which is a major component of blood and is known to bind a variety of charged solutes like sodium, calcium, magnesium and hydrogen ions. The extended model may also consider that each albumin molecule may bind a large number of these ions with different equilibrium constants and that this binding is pH dependent. In a further example, the extended model may consider complexes formed when calcium and magnesium bind to bicarbonate and citrate.

For the transport algorithm, the membrane 11a may be considered to be composed of a number of serial segments. For each membrane segment, the transport of each solute and each complex may be calculated separately, taking the membrane potential into account. With the given inlet concentration for each solute, the outlet concentrations for a membrane segment may be calculated from the transports. The total concentration of each compound may be calculated by summing the free concentration and the concentrations of all complexes where they appear. From the total concentration, a new distribution between free concentration and relevant complexes may be calculated. The recalculated concentration may be used as input to the next membrane segment. This calculation is done iteratively along the whole membrane 11a until a steady state situation is reached.

The skilled person understands that the extended model may be derived in many different ways and the foregoing is merely to be regarded as guiding principles. In any event, the extended model results in a non-linear system of equations, which may be numerically solved to render an extended function $f\_iCa_{ext}$ that gives ionized calcium at any location in the EC circuit 10 as a function of modeled substances at this location.

In one example, the extended model is configured to handle 26 chemical reactions and, after adding equations for totals of involved substances including calcium and electroneutrality, the extended model results in a non-linear system of 37 equations. The extended function $f\_iCa_{ext}$ may be a function of variables such as totals of calcium, magnesium, sodium, chloride, potassium, bicarbonate, hydrogen phosphate, sulfate, citrate, acetate, lactate and albumin.

The extended model may also result in an equation for the total calcium at loc2, i.e. $Ca_2$, e.g. by considering mass flow balance between loc1 and loc3, and losses in the dialyzer 11 between loc3 and loc2. In one example, such an equation is given by:

$$Ca_{PW2} = (Q_{PLASMA} - K_{Ca} \cdot F_{CAL} \cdot F_{DIL} \cdot Ca_{SYS}) \cdot \left(\frac{1}{Q_{PWI} - Q_{FIL}}\right)$$

where $K_{Ca}$ is the clearance of calcium in the dialyzer 11, $F_{CAL}$ may be approximated by a constant number (e.g. in range 0.8-1), and $$Q_{PLASMA} = (1 - H) \cdot Q_B \cdot 60$$

$$F_{DIL} = \frac{Q_{PW}}{Q_{PWI}}$$

$$Q_{PWI} = Q_{PW} + Q_{PBP} + Q_{PRE}$$

$$Q_{PW} = (1 - H) \cdot fpw \cdot Q_B \cdot 60$$

$$Q_{FIL} = Q_E - Q_D$$

Further, $Ca_2$ may be obtained from $Ca_{PW2}$ by straight-forward conversion:

$$Ca_2 = Ca_{PW2} \cdot fpw_2$$

where $$fpw_2 = 1 - \frac{Q_B \cdot 60 \cdot (1 - H)}{(1 - H_2) \cdot (60 \cdot Q_B + Q_{PBP} + Q_{PRE} - Q_{FIL}) \cdot (1 - fpw)}$$

$$H_2 = Q_B * 60 * \frac{H}{Q_B * 60 + Q_{PBP} + Q_{PRE} - Q_{FIL}}$$

Thus, in this example, an equation for the total calcium at loc2 may be given as a second function $Ca_2 = f_{o,2}(Ca_{SYS}, H, fpw, K_{Ca}, F_{CAL}, Q_B, Q_{PRE}, Q_E, Q_D, Q_{PBP})$.

The extended model may also result in an equation for the total citrate at loc2, i.e. $CIT_2$, e.g. by considering mass flow balance between loc1 and loc3, and losses in the dialyzer 11 between loc3 and loc2. In one example, such an equation is given by:

$$CIT_{PW2} = (D_{CIT} \cdot Q_B \cdot 60) + (CIT_{SYS} \cdot Q_{PLASMA}) \cdot \left(1 - \frac{K_{CIT}}{Q_{PWI}}\right) \cdot \left(\frac{1}{Q_{PWI} - Q_{FIL}}\right)$$

In this example, citrate dose $D_{CIT}$ is given in mmol/L and defined by the equation:

$$D_{CIT} = \frac{CIT_{PBP} \cdot Q_{PBP}}{Q_B \cdot 60}$$

where $CIT_{PBP}$ is the citrate concentration in source 22.

It is understood that $CIT_2$ may be obtained from $CIT_{PW2}$ by straight-forward conversion:

$$CIT_2 = CIT_{PW2} \cdot fpw_2$$

Thus, in this example, an equation for the total citrate at loc2 may be given as a third function $CIT_2 = f_{o,3}(CIT_{sys}, H, fpw, K_{CIT}, D_{CIT}, Q_B, Q_{PRE}, Q_E, Q_D, Q_{PBP})$.

As seen, $f_{o,3}$ depends on the total citrate in the patient's blood, $CIT_{SYS}$. In one embodiment, $CIT_{SYS}$ may be set to a fixed value. However, it has been found that improved results may be achieved by instead modeling $CIT_{SYS}$ as a function of treatment time. Such modeling may be performed in many different ways. One example is described in the article "*Citrate Pharmacokinetics in Critically Ill Patients with Acute Kidney Injury*", by Zheng et al., published in PLoS One Vol. 8,6 (2013). An equation for the systemic total citrate as a function of time may be given by:

$$CIT_{SYS} = CIT_0 \cdot e^{-(K_{CIT}/1000 + K_{BODY})\left(\frac{t}{V_D}\right)} + (J_{CITLOAD} + G_{MET}) \cdot$$

$$\left(\frac{1}{K_{CIT}/1000 + K_{BODY}}\right) \cdot \left(1 - e^{-(K_{CIT}/1000 + K_{BODY})\left(\frac{t}{V_D}\right)}\right)$$

where $CIT_0$ is the level of systemic total citrate at the start of RCA and may be set to a predefined or measured value, and t is the time from start of RCA, and $J_{CITLOAD} = D_{CIT} * Q_B * 60 * 10^{-3}$. This equation accounts for the rate of body metabolism of citrate ($G_{MET}$) and also accounts for the infusion of citrate into the EC circuit 10 and the loss (clearance) of total citrate in the dialyzer 11.

Although not shown herein, the model may be modified to account for an abnormal metabolic rate in the patient, e.g. by modifying the parameter $G_{MET}$.

Thus, in this example, an equation for the systemic total citrate may be given as a fourth function $CIT_{SYS}=f_{0,4}(CIT_0, V_D, K_{BODY}, G_{MET}, D_{CIT}, Q_B, K_{CIT}, t)$ As understood from the foregoing, the extended model may also include one or more equations for calculation of the clearance of total citrate and total calcium in the dialyzer. Such equations are well-known in the art and the clearance for substance Y may be represented as a fifth function $K_Y=f_{0,5}(k_0A_Y, \alpha_Y, Q_B, Q_D, Q_{FIL})$.

The extended model may also comprise an equation for conversion of systemic ionized calcium, $iCa_{SYS}$, to systemic total calcium, $Ca_{SYS}$. Such an equation may be derived by considering $Ca_{SYS}$ as the sum of the different forms of calcium in plasma, e.g. iCa, CaAlb, CaHCO3, CaPO4, CaCit and CaCit2. The model may quantify each form by considering its chemical equilibrium. For example, $CaCit=iCas_{SYS} \cdot iCIT \cdot EQ_{Cacit}$, where CaCit and iCIT are the concentration of CaCit and ionized citrate, respectively, and $EQ_{Cacit}$ is the equilibrium association constant for CaCit. Further, the model may account for the fact that albumin has 12 binding sites that may be occupied by free calcium, and that the number of occupied binding sites ($nCa_{REF}$) is dependent on pH:

$$nCa_{REF}=1.58+0.907 \cdot (pH-7.4)$$

In one example, an equation for the systemic total calcium may be given by:

$$Ca_{SYS} = iCa_{SYS} \cdot \left(1 + 12 \cdot \frac{Alb}{(EQ_{Ca} + iCa_{SYS})}\right) + \frac{HCO_3}{1000} \cdot EQ_{CaHCO_3} + \frac{HCO_3}{1000 * 10^{-\frac{pH}{EQ_{CaCO_3}}}} + \frac{iP \cdot EQ_{CaPO_4}}{1000} + \frac{iCIT \cdot EQ_{CaCIT}}{1000} + \frac{iCIT \cdot \frac{iCIT \cdot EQ_{CaCIT2}}{1000}}{1000}$$

where $EQ_{CaHCO_3}$, $EQ_{CaCO_3}$, $EQ_{CaPO_4}$, $EQ_{CaCIT}$, $EQ_{CaCIT2}$ may be taken from handbooks, and $EQ_{Ca}$ may be calculated as:

$$EQ_{Ca} = iCa_{REF} * \left(\frac{12}{nCa_{REF}} - 1\right)$$

with $iCa_{REF}=1.25$ mmol/L.

Thus, in this example, an equation for the systemic total calcium may be given as a sixth function $Ca_{SYS}=f_{0,6}(iCa_{SYS}, Alb, HCO_3, pH, EQ_{CaX}, iCIT, iCa_{REF}, iP)$, where $EQ_{CaX}$ represents the equilibrium association constants $EQ_{Ca}$, $EQ_{CaHCO_3}$, $EQ_{CaCO_3}$, $EQ_{CaPO_4}$, $EQ_{CaCIT}$, $EQ_{CaCIT2}$.

Reverting now to FIG. 4, it is seen that the extended computation function $f\_iCa_{ext}$ and the second to sixth computation functions $f_{0,2}$, $f_{0,3}$, $f_{0,4}$, $f_{0,5}$, $f_{0,6}$ are provided to block 401, in which a reduced model is determined to define the predefined algorithm for use in the RCA monitoring.

One reason for block 401 is that full solving of $f\_iCa_{ext}$ requires significant computing capacity. In an attempt to reduce the complexity of $f\_iCa_{ext}$, the inventors have made computer simulations which indicate that the extended function has a major dependence on the totals for calcium and citrate, and a smaller dependence on other variables. Therefore, to simplify computations, $f\_iCa_{ext}$ may be linearized with respect to the variables of total calcium ($Ca_x$) and total citrate ($CIT_x$), where subscript x denotes an arbitrary location in the EC circuit 10:

$$f_{0,1}(Ca_x, CIT_x) = f\_iCa_{ext}(Ca_{REF}, CIT_{REF}) + \frac{\delta f\_iCa_{ext}}{\delta Ca_x}(Ca_{REF}, CIT_{REF}) \cdot (Ca_x - Ca_{REF}) + \frac{\delta f\_iCa_{ext}}{\delta CIT_x}(Ca_{REF}, CIT_{REF}) \cdot (CIT_x - CIT_{REF})$$

Figure 5:
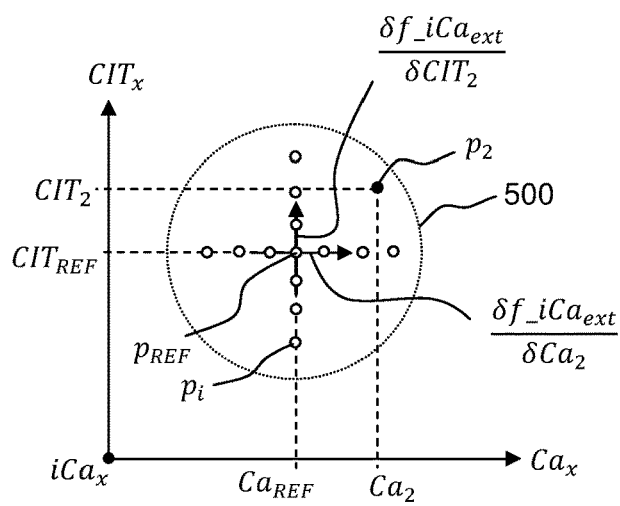
FIG. 5 illustrates linearization of an extended function for calculating post-dialyzer ionized calcium.

The linearization is further illustrated in FIG. 5 which schematically depicts a three-dimensional space which is spanned by the dimensions $iCa_x$, $Ca_x$, and $CIT_x$, and where different evaluation points $p_i$ are indicated by open circles. Each evaluation point pi is given by a pair of coordinates in the $Ca_x$ and $CIT_x$ dimensions. Specifically, the extended function $f\_iCa_{ext}$ is evaluated at evaluation points $p_i$ selected around and including a reference point $p_{REF}$, which is given by reference values for total calcium ($Ca_{REF}$) and total citrate ($CIT_{REF}$). The reference values are selected to be relevant at the post-dialyzer location, loc2, and may be nominal (desired) values at this location. As indicated in FIG. 5, the derivative of $f\_iCa_{ext}$ in the $Ca_x$ dimension ($\delta f\_iCa_{ext}/\delta Ca_x$) and in the $CIT_x$ dimension ($\delta f\_iCa_{ext}/\delta CIT_x$) at the reference point $p_{REF}$ may be estimated based on the evaluated values of $f\_iCa_{ext}$ at a number of evaluation points $p_i$ in the $Ca_x$ dimension and the $CIT_x$ dimension, respectively. The linearized function $f_{0,1}$ makes it possible to compute ionized calcium at loc2, i.e. $iCa_2$, based on current values of total citrate, $CIT_2$, and total calcium, $Ca_2$, at loc2, represented by $P_2$ in FIG. 5. The linearization may also involve comparing the outputs of $f_{0,1}$ and $f\_iCa_{ext}$ to verify that a sufficient agreement is achieved within a region of interest 500, i.e. for all relevant values of total calcium and total citrate at loc2.

The values of parameters included in the extended function, $f_{iCa_{ext}}$, other than the modeled parameters may be estimated based on experience and/or be taken from literature and handbooks and/or be obtained for a relevant population of patients. In the latter example, at least some of the parameter values may be obtained as an average of a respective machine setting or measured physiological parameter, e.g. for a specific clinic, group of clinics, etc. Thereby, the extended function may be tailored to a specific environment.

To summarize, and as indicated in block 401 in FIG. 4, the linearization may be seen to result in a linear function for calculating iCa based on Ca and CIT in loc2:

$$iCa_2=f_{0,1}(Ca_2,CIT_2)=\beta_0+\beta_1 \cdot (Ca_2-Ca_{REF})+\beta_2 \cdot (CIT_2-CIT_{REF})$$

where $\beta_0$, $\beta_1$ and $\beta_2$ are constants given by the linearization. In one example, $iCa_2$ is calculated in mmol/L and the parameters of $f_{0,1}$ are given by $\beta_0$=[0.32, 0.45], $\beta_1$=[0.29, 0.41], $\beta_2$=[−0.15, −0.05], $Ca_{REF}$=[1.15,1.55] and $CIT_{REF}$= [2.00, 2.80], where the respective pair of brackets defines an interval which is inclusive of the start and end values.

FIG. 10 contains a summary overview of the functions $f_{0,1}$-$f_{0,6}$ as well additional functions described further below.

Block 401 may also involve defining one or more final functions to be used in the algorithmic computations by block 410. For example, as indicated in block 401, the computation functions $f_{0,1}$, $f_{0,2}$, $f_{0,3}$, $f_{0,5}$, $f_{0,6}$ may be combined into an aggregated computation function that directly outputs post-dialyzer ionized calcium, $iCa_2$, based on measured values of systemic ionized calcium and systemic total citrate: $iCa_2 = f_1(iCa_{SYS}, CIT_{SYS})$. The use of an aggregated function is optional; post-dialyzer ionized calcium, $iCa_2$ may instead be computed by evaluating $f_{0,1}$, $f_{0,2}$, $f_{0,3}$, $f_{0,5}$, $f_{0,6}$ in suitable sequence based on measured values of $iCa_{SYS}$. Thus, any reference to $f_1$ in the following may imply the aggregated function or the sequence of functions $f_{0,1}$, $f_{0,2}$, $f_{0,3}$, $f_{0,5}$, $f_{0,6}$ or any composite functions formed therefrom.

Block 401 may also involve assigning one or more fixed generic values, which are presumed valid for the relevant systems 1, modalities and patients, to one more parameters that are used in the above-mentioned functions. Such parameter(s) may be constant and, e.g., include one or more of $F_{CAL}$, H, fpw, $CIT_0$, $G_{MET}$, $K_{BODY}$, $V_D$, $k_0A_y$, $α_y$, Alb, $HCO_3$, pH, $EQ_{Cax}$, iCIT, $iCa_{REF}$ and iP. It is also conceivable that block 401 involves defining one or more approximation functions for estimating one or more parameters in dependence of a measurable property of the patient 100. Such approximation function(s) may, e.g., include one or more of: $G_{MET}=0.0167·W$, $V_D=(29/72)·W$ and $K_{BODY}=7.79·W·60·10^{-3}$, where W is the weight of the patient.

In the example of FIG. 4, block 401 also involves defining (e.g., based on $f_{0,6}$) a final function for computing systemic total calcium based on systemic ionized calcium: $Ca_{SYS}=f_2(iCa_{SYS})$, and defining (e.g., based on $f_{0,4}$) a final function for estimating systemic total citrate as a function of time: $CIT_{SYS}=f_3(t)$.

As shown in FIG. 4, block 401 provides a set of computation functions $f_1$, $f_2$, $f_3$ to the computation module 410, in which the set of functions $f_1$, $f_2$, $f_3$ forms the core of a predefined algorithm for computation of post-dialyzer ionized calcium, $iCa_2$, and optionally further parameters. In the illustrated example, the predefined algorithm comprises the functions:

$$\begin{cases} iCa_2 = f_1(iCa_{SYS}, CIT_{SYS}) \\ Ca_{SYS} = f_2(iCa_{SYS}) \\ CIT_{SYS} = f_3(t) \\ R_{Ca} = Ca_{SYS}/iCa_{SYS} \end{cases}$$

where $R_{Ca}$ is the calcium ratio which is conventionally used for evaluating citrate accumulation during RCA, as explained in the Background section. It should be noted that the dependence of the respective function on various parameters is not exhaustive. For example, as understood from the foregoing, the function $f_1$ depends on several additional parameters, such as flow rates, clearances, etc. Likewise, function $f_2$ several additional parameters, such as concentrations of albumin and bicarbonate in the patient's blood, pH of the patient's blood, etc.

The computation module 401 operates the predefined algorithm on current measurement data 402. In the illustrated example the measurement data 402 is a measured value of $iCa_{SYS}$, which is typically measured at loc1 in FIG. 2. The computation block 410 also operates on further input data, which includes one or more current values of machine settings (MS) 403 of the blood treatment system 1, and may also include one or more physiological parameters (PP) 404 of the patient 100, one or more system parameters (SP) 405 relating to the configuration of the system 1, and one or more chemical parameters (CP) 406. Examples of such parameters are given in the table of FIG. 6. As used herein, "machine settings" are current values of operation parameters for the blood treatment system 1, "physiological parameters" define the physiological state of the patient 100 or a group of representative patients, "system parameters" define the current structural configuration of the blood treatment system 1, and "chemical parameters" define chemical characteristics of blood.

Some of the parameters in FIG. 6 may be considered as constants. Generic values of such constants may be pre-stored in memory (cf. 42 in FIG. 1) for retrieval by the module 410. Alternatively, as explained above, generic values of one or more constants may instead be embedded in the set of functions $f_1$, $f_2$, $f_3$.

The values of at least some of the parameters in FIG. 6 may be entered by the operator of the system 1 before start-up of a blood treatment session or, depending on implementation, may be calculated by the control device (40 in FIG. 1) before and/or during the blood treatment session. Such parameters may include one or more machine settings (MS), e.g. one or more of treatment time, total fluid to be removed from the patient, blood flow rate ($Q_B$), dialysis fluid flow rate ($Q_D$), effluent flow rate ($Q_E$), flow rate of replacement fluid upstream of dialyzer ($Q_{PRE}$), flow rate of replacement fluid downstream of dialyzer ($Q_{POST}$), ultrafiltration rate ($Q_{FIL}$), flow rate of citrate-containing fluid ($Q_{PBP}$), citrate dose ($D_{CIT}$), etc. It is also conceivable that block 410 obtains one or more machine settings from sensor(s) in the system 1, e.g. flow rate sensor(s), pump speed sensor(s), etc. It should be noted that one or more of the machine settings (MS) may be changed, by the operator or the control device, during the treatment session and that the computation block 410 is configured to account for such changes by entering the changed parameter values into the predefined computation algorithm.

The operator may also enter current values of patient parameters (PP), such as hematocrit (H), albumin concentration (Alb), bicarbonate concentration ($HCO_3$), weight (W), blood pH (pH), etc. Concentration values and pH may be given by laboratory analysis of the patient's blood and may alternatively pre-stored in the memory (42 in FIG. 1) for subsequent retrieval.

With respect to the examples of system parameters (SP) in FIG. 6, it may be noted that the clearance parameters $K_{Ca}$, $K_{CIT}$ may be included in input data in so far as they are fixed values rather than calculated by the function $f_{0,5}$. In addition to the parameter examples in FIG. 6, the operator may also indicate the type of fluid within one or more of the sources 13, 20, 21, 22, 23 (FIG. 2), so that the composition of the fluid is known to block 410. For example, the predefined algorithm may be configured to account for the concentration of calcium or citrate, if present in any of the fluids.

The system in FIG. 4 may implement the RCA monitoring 300 of FIG. 3. Thus, the computation module 410 may be configured to obtain the current measurement data 402, which represents a current measured value of systemic ionized calcium ($iCa_{SYS}$) in accordance with step 301. Module 410 may be further configured to compute and output one or more current computation values, including a current value of post-dialyzer ionized calcium ($iCa_2$), by operating the predefined algorithm on the measurement data 402 and the further input data 403-406. As indicated in FIG. 4, output data from the module 410 may additionally include one or more of a current value of systemic total calcium ($Ca_{SYS}$), a current value of systemic total citrate ($CIT_{SYS}$), a current value of the calcium ratio ($R_{Ca}$), and the current measured value of systemic ionized calcium ($iCa_{SYS}$).

The system in FIG. 4 further comprises a monitoring module 420, which is configured to receive the output data from the computation module 410 and perform one or more monitoring operations based thereon, e.g. in accordance with step 303 in FIG. 3. In the illustrated example, the monitoring module 420 comprises a decision support sub-module 421, a presentation sub-module 422 and a safety check module 423.

The decision support module 421 is configured to obtain a predefined and clinically proven protocol 407 for blood treatment combined with RCA. The protocol 407 may be tailored to the current blood treatment system 1, such as its modality and the compositions of the fluids, and may define the type of dialyzer(s) that may be used, allowable ranges of individual machine settings, etc. Further, the protocol 407 may define acceptable range(s) for the output data from the module 410, as well as corrective measures to be taken when the output data falls outside the acceptable range(s). Protocols for blood treatment combined with RCA are defined based on experience and extensive testing. There are many available treatment protocols, including universal protocols such as the so-called Kalmar protocol, e.g. described in the article "*Regional Citrate Anticoagulation in Continuous Renal Replacement Therapies*", by Daga-Ruiz et al, published in Int J Crit Care Emerg Med 2018, 4:054, or local protocols defined by or for a specific clinic or clinic provider. The decision support module 421 comprises logic which is configured to process the protocol 407 to define a set of rules that associates ranges of output values, such as one or more of $iCa_2$, $Ca_{SYS}$, $iCa_{SYS}$, $R_{Ca}$ and $CIT_{SYS}$ with corrective measures to be taken. The logic is further configured to compare the output data from the module 410 with the set of rules and, based on the comparison, determine if and how any settings of the system 1 should be modified to improve the performance of the RCA. Based thereon, the module 421 may output one or more operational recommendations 408 for presentation to the operator, e.g. on the display device 45. The recommendation(s) 408 may, e.g., indicate one or more machine settings to be changed and a desired direction or amount of change.

The presentation sub-module 422 is configured to format and provide the output data for presentation on a display device 45. For example, the output data may be presented to show current values and/or trends to the operator.

The safety check module 423 is configured to compare the output data to one or more operational limits, which may be predefined and stored in memory or given by the protocol 407, and to cause an alarm device 430 to generate an audible and/or visible alarm signal whenever a deviation between the output data and the operational limit(s) is detected. Concurrently, the safety check module 423 may cause the system 1 to enter a safe operational mode, which is configured to safeguard the patient's health.

It is also conceivable to combine the monitoring module 420 with a control module so that the system in FIG. 4 is also configured to automatically determine suitable changes to machine settings based on the output data, e.g. in view of the protocol 407, and modify one or more of control signals for the blood treatment system 1 accordingly (cf. signals S1-S7 in FIG. 1), possibly subject to confirmation by the operator through use of the input device 44.

Figure 7:
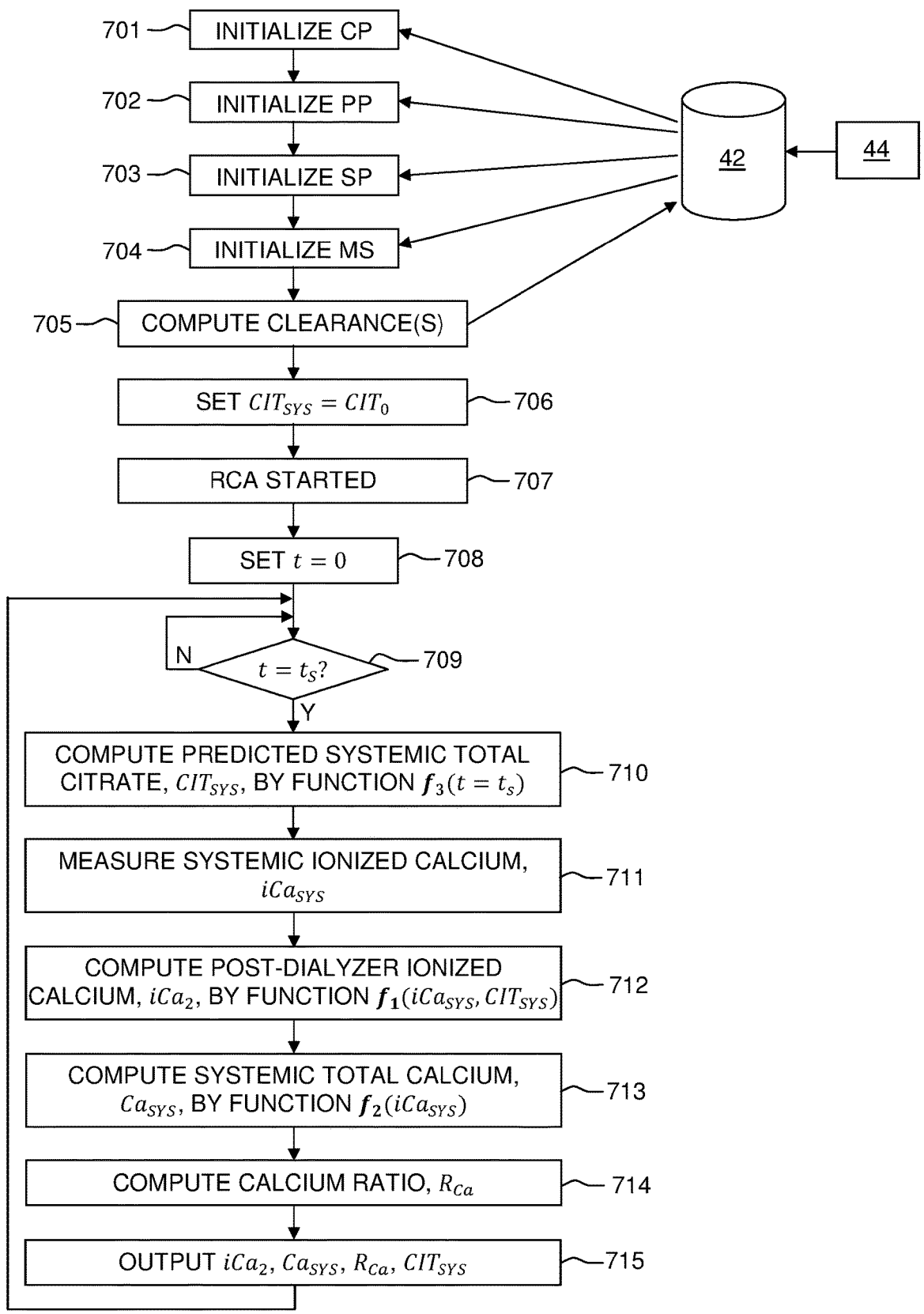
FIG. 7 is a flow chart of an example computation method performed by the system of FIG. 4.

FIG. 7 is a flow chart of a computation method that may be performed by the computation module 410 in FIG. 4, e.g. when implemented on the device 40 in FIG. 1. In steps 701-704, chemical parameters CP, physiological parameters PP, system parameters SP and machine settings MS are initialized, in which corresponding variables are instantiated and assigned a value. In the illustrated example, the values have been entered via the input device 44 and stored in the memory 42, from which the values are read in steps 701-704. As understood from the foregoing discussion, some values may be entered well ahead of blood treatment, e.g. during configuration of the device 40, while other values may be entered by the operator in preparation for a specific treatment session. In step 705, the clearances of calcium and citrate ($K_{Ca}$, $K_{CIT}$) are calculated, e.g. by use of function $f_{0,5}$ or any equivalent function. In a variant, these clearances are set equal and calculated for one of calcium and citrate. In yet another variant, fixed values of $K_{Ca}$, $K_{CIT}$ are included among the system parameters. In step 706, the systemic total citrate $CIT_{SYS}$ is set to $CIT_0$. The computation method is now prepared for performing computations as part of the RCA monitoring during a blood treatment session.

After being notified that RCA has started (step 707), a counter of the treatment time (t) is set to zero in step 708. In step 709, the computation method waits until the treatment time equals a sampling time point ($t_S$). At this time, the method proceeds to step 710 which computes a predicted value of systemic total citrate at the sampling time point, by evaluating function $f_3$ at $t=t_S$. In step 711, a measured value of systemic ionized calcium $iCa_{SYS}$ is obtained, either by user input via the input device 44, or from the blood analysis apparatus 50 over the connection 52 (FIG. 1). In step 712, a value of post-dialyzer ionized calcium $iCa_2$ is computed by operating the function $f_1$ on the measured $iCa_{SYS}$ value and the predicted $CIT_{SYS}$ value (given by step 710). In step 713, a current value of systemic total calcium $Ca_{SYS}$ is computed by operating function $f_2$ on the measured $iCa_{SYS}$ value. In step 714, the calcium ratio $R_{Ca}$ is computed based on the current values of $iCa_{SYS}$ and $CIT_{SYS}$. In step 715, the current values of $iCa_{SYS}$, $iCa_2$, $Ca_{SYS}$, $R_{Ca}$ and $CIT_{SYS}$ are output, whereupon the method returns to step 709, to wait for the next sampling time point. In one embodiment, the sampling time points are predefined and, e.g., given by a data structure stored in the memory 42. Alternatively or additionally, the next sampling time point may be implied whenever a measured $iCa_{SYS}$ value is obtained (cf. step 711).

FIG. 8A graphically depicts the sequence of calculations that may be performed during execution of the computation method in FIG. 7. Open circles represent measured values, filled circles represent computed values, and arrows indicate the values used in the respective calculation. The graph in FIG. 7A presumes that measurements are taken every hour for the first three hours and then every fourth hour. At each such measurement (sampling time point), a current value of $CIT_{SYS}$ is projected and used, together with the measured value of $iCa_{SYS}$, for computing a current value of $iCa_2$. The measured value of $iCa_{SYS}$ is further used for computing a current value of $Ca_{SYS}$ which is used, together with measured value of $iCa_{SYS}$, for computing a current value of $R_{Ca}$. In the illustrated example, it is presumed that the current value of $CIT_{SYS}$ is projected based on the preceding value of $CIT_{SYS}$. In an alternative, using function $f_3$, current values of $CIT_{SYS}$ are projected based on the value of $CIT_{SYS}$ at time $t=t_0$ ($CIT_0$).

As explained with reference to FIG. 3, steps 301-302 may alternatively obtain a measured value of systemic total calcium, $Ca_{SYS}$, and compute a current value of post-dialyzer ionized calcium, $iCa_2$, based on the measured value of $Ca_{SYS}$. Such an embodiment may be implemented by modification of the system in FIG. 4, in which the measurement data 402 is $Ca_{SYS}$ instead of $iCa_{SYS}$. The computation of a current value of $iCa_2$ based on a measured value of $Ca_{SYS}$ may be implemented in different ways. A few non-limiting examples are given below.

In a first example, a seventh function $f_{0,7}$ is provided to generate $iCa_{SYS}$ as a function of $Ca_{SYS}$, by straight-forward re-arrangement of variables in function $f_{0,6}$:

$$iCa_{SYS} = f_{0,7}(Ca_{SYS}, Alb, HCO_3, pH, EQ_{CaX}, iCIT, iCa_{REF}, iP)$$

In the first example, with reference to FIG. 4, block 401 may be seen to involve defining, based on $f_{0,7}$, a final function for computing systemic ionized calcium based on systemic total calcium: $iCa_{SYS} = f_4(Ca_{SYS})$ and providing the set of functions $f_1$, $f_3$, $f_4$ to the computation module 410. The computation method in FIG. 7 may be modified accordingly, by step 711 obtaining a measured value of $Ca_{SYS}$, step 712 computing a value of $iCa_{SYS}$ by operating the function $f_4$ on the measured value of $Ca_{SYS}$, and step 713 computing a value of $iCa_2$ operating the function $f_1$ on the computed value of $iCa_{SYS}$ and the predicted value of $CIT_{SYS}$ (given by step 710). FIG. 8B graphically depicts the sequence of calculations that may be performed during execution of such a modified computation method.

In a second example, with reference to FIG. 4, block 401 may be seen to involve combining functions $f_{0,1}$, $f_{0,2}$, $f_{0,3}$, $f_{0,5}$ into a final function for computing post-dialyzer ionized calcium based on systemic total calcium and systemic total citrate: $iCa_2 = f_1^*(Ca_{SYS}, CIT_{SYS})$ and to provide the set of functions $f_1^*$, $f_3$, $f_4$ to the computation module 410.

In a third example, block 401 may be seen to involve a further linearization of function $f\_iCa_{ext}$ to derive a linear function $f_{0,7}^*$ for calculating systemic iCa based on systemic Ca and systemic CIT. The linearization may be performed as exemplified with reference to FIG. 5 but at a reference point $P_{REF\_2}$ given by reference values for total calcium ($Ca_{REF\_2}$) and total citrate ($CIT_{REF\_2}$) in the blood of the patient. Such a linear function may be given by:

$$iCa_{SYS} = f_{0,7}^*(Ca_{SYS}, CIT_{SYS}) = \beta_{0\_2} + \beta_{1\_2} \cdot (Ca_{SYS} - Ca_{REF\_2}) + \beta_{2\_2} \cdot (CIT_{SYS} - CIT_{REF\_2})$$

where $\beta_{0\_2}$, $\beta_{1\_2}$ and $\beta_{2\_2}$ are constants given by the linearization. By analogy with function $f_1$, functions $f_{0,2}$, $f_{0,3}$, $f_{0,4}$, $f_{0,5}$, $f_{0,7}^*$ may be seen to form a final function $iCa_{SYS} = f_4^*(Ca_{SYS}, CIT_{SYS})$. Thus, in the third example, block 401 may provide the set of functions $f_1$, $f_3$ $f_4^*$ or $f_1^*$, $f_3$, $f_4^*$ to the computation module 410.

Figure 9A:
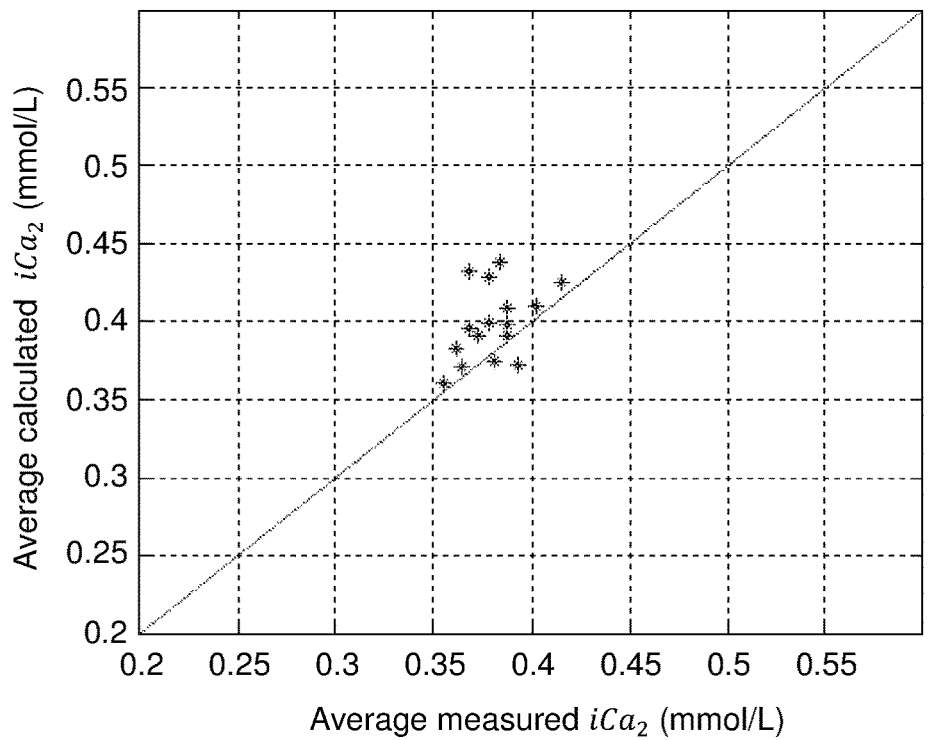
FIG. 9A is a graph of time averages of calculated and measured post-dialyzer ionized calcium for a plurality of patients.
Figure 9B:
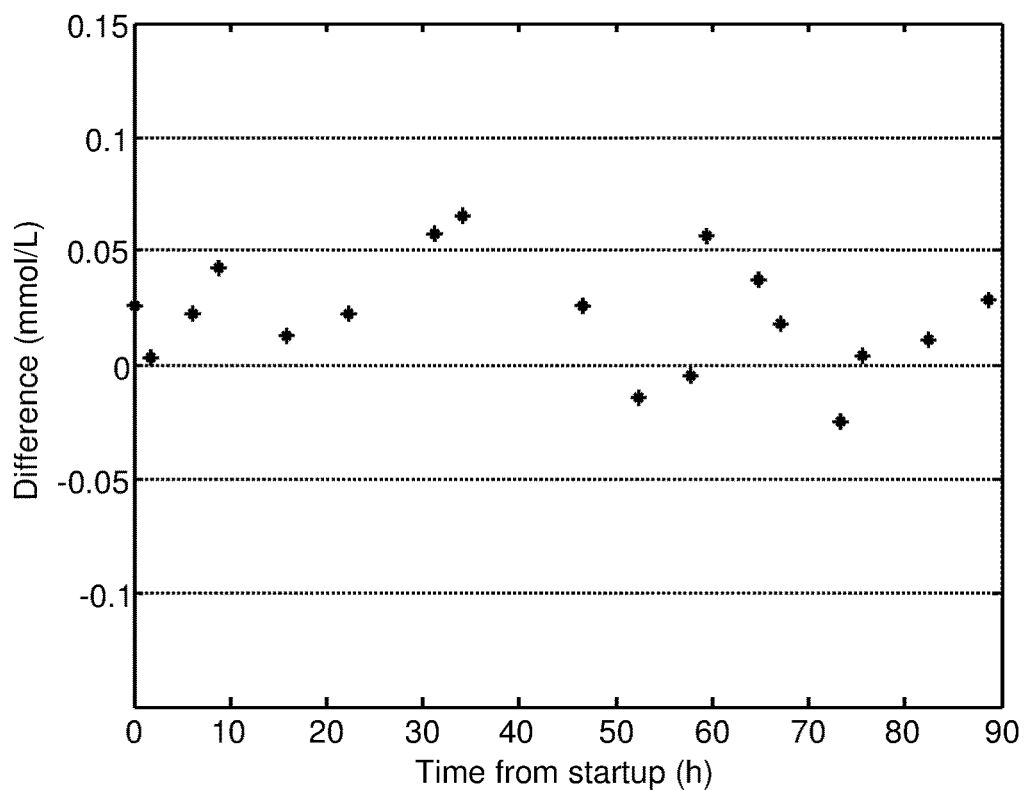
FIG. 9B is a graph of a time series of difference values between calculated and measured values of post-dialyzer ionized calcium for one patient.
Figure 9C:
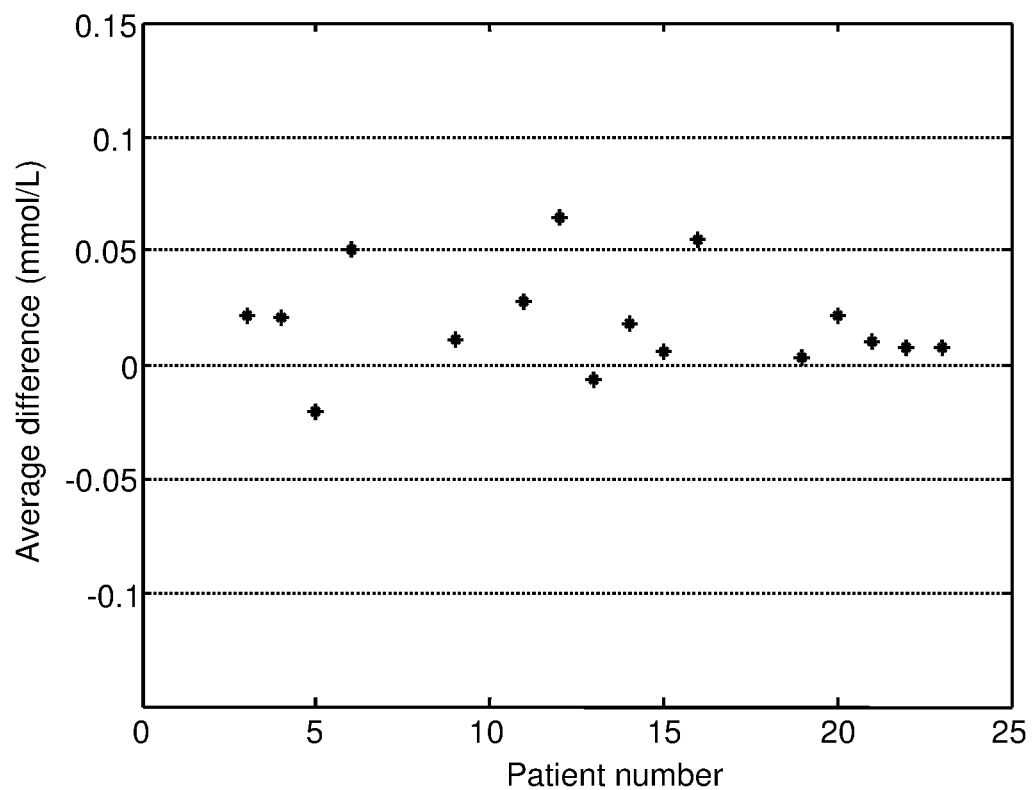
FIG. 9C is a graph of the time average of difference values between calculated and measured values of post-dialyzer ionized calcium for each of a plurality of patients.
Figure 9D:
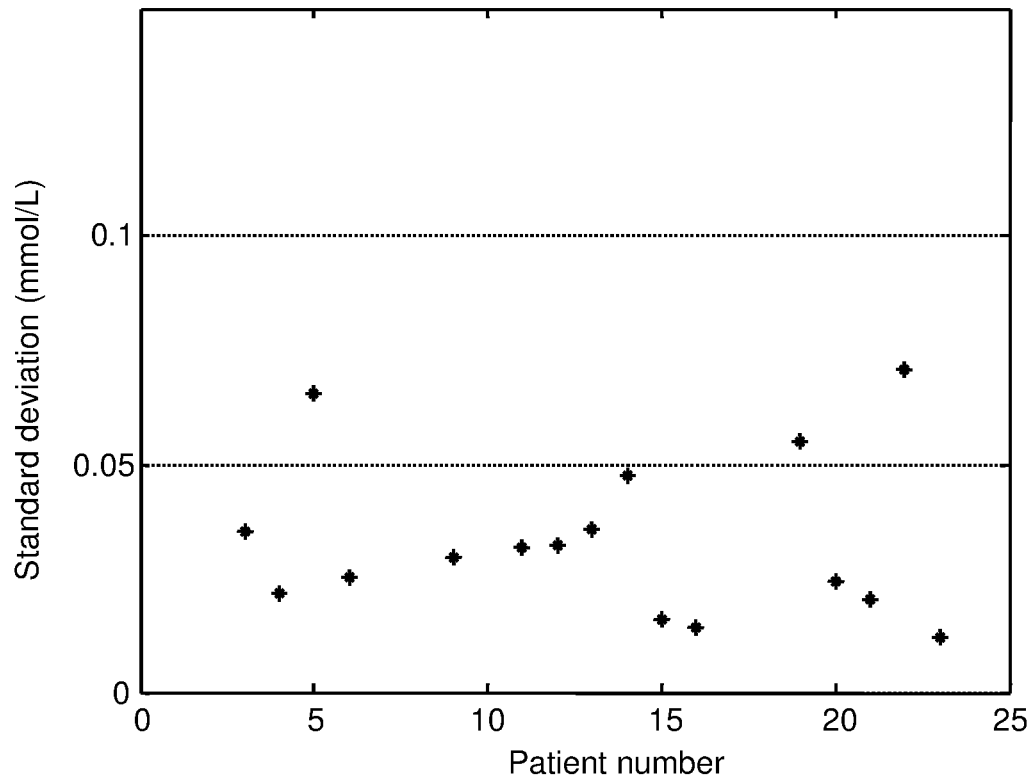
FIG. 9D is a graph of the standard deviation of difference values between calculated and measured values of post-dialyzer ionized calcium for each of a plurality of patients.

The utility of the computation method in FIG. 7 has been evaluated based on measurement data obtained for a plurality of patients when subjected to blood treatment by CRRT machines (Prismaflex® from Baxter Corporation) equipped with ST150 sets and operated predominantly in modality CVVHDF. Values of post-dialyzer ionized calcium, $iCa_2$, were computed based on measured values of systemic ionized calcium, $iCa_{SYS}$, and compared to measured values of post-dialyzer ionized calcium. The measured values were obtained by blood sampling and BGA analysis as described with reference to FIG. 1. FIG. 9A is a comparison of average computed $iCa_2$ values versus average measured $iCa_2$ values, where each data point in FIG. 9A represents time averages of computed and measured values, respectively, for a respective patient. FIG. 9B shows an example of the difference between individual computed and measured $iCa_2$ values during a treatment session. FIG. 9C is a graph of the average difference between computed and measured $iCa_2$ values for a plurality of patients. The average of the data points in FIG. 9C is 0.013 mmol/L with a standard deviation of 0.019 mmol/L. FIG. 9D is a graph of the standard deviation of the difference between computed and measured $iCa_2$ values for the plurality of patients in FIG. 9C. Considering that a standard BGA typically has an nominal accuracy of ±7.5% and that BGAs are not certified for measurements of ionized calcium in the range of 0.2-0.5 mmol/L or for blood samples with high concentration of citrate, the results in FIGS. 9A-9D indicate that the computation method is useful for replacing measurements of post-dialyzer ionized calcium in systems for blood treatment that involves RCA.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments. Reverting to FIG. 4, block 400 may not only represent a preparatory step for defining the extended model, but may be an operative module which is configured to adapt the extended model based on measurement data M, as indicated by dashed lines in FIG. 4, where the measurement data M is obtained at considerably lower rate than the input data 402. The measurement data M may comprise measured amounts of one or more forms of calcium, total calcium, or total citrate in the blood of the patient and/or in the blood at any location in the EC circuit 10. In one example, the measurement data M may include measured $Ca_{SYS}$ values, and block 400 may adjust the function $f_{0,6}$ by comparing the measured $Ca_{SYS}$ values to computed $Ca_{SYS}$ values, which are obtained by operating $f_{0,6}$ on measured $iCa_{SYS}$ values (cf. input data 402). In another example, the measurement data M may include measured $CIT_{SYS}$ values, and block 400 may adjust the function $f_{0,4}$ by comparing the measured $CIT_{SYS}$ values to computed $Ca_{SYS}$ values given by $f_{0,4}$ as a function of treatment time. In yet another example, the measurement data M may include measured $iCa_2$ values and measured $Ca_2$ values, and block 400 may adjust the extended function $f\_iCa_{ext}$, by comparing the measured $iCa_2$ values to computed $iCa_2$ values, which are obtained by operating $f\_iCa_{ext}$ on the measured $Ca_2$ values.

Correspondingly, as also indicated in FIG. 4, block 401 may be an operative module which is configured to adapt the reduced model based on measurement data M, e.g. by adjusting any one of functions $f_1$, $f_1^*$, $f_2$, $f_3$, $f_4$, $f_4^*$.

It may also be noted that the linear function $f_{0,1}$ need not be derived, in block 401, by linearization of an extended function given by theoretical modeling of the system 1 but may instead be derived by linear regression analysis of time-coordinated measurement values of $iCa_2$, $Ca_2$ and $CIT_2$. Correspondingly, the linear function $f_{0,7}^*$ may be derived by linear regression analysis of time-coordinated measurement values of $iCa_{SYS}$, $Ca_{SYS}$ and $CIT_{SYS}$. In a further variant, the extended model includes a respective extended function for each relevant form of calcium in the blood, including ionized calcium and one or more of CaAlb, CaHCO3, CaPO4, CaCit and CaCit2. Correspondingly, the reduced model may include a respective linear function for each relevant form, where the respective linear function is obtained by linearization of the respective extended function with respect to variables Ca and CIT (cf. FIG. 5). The reduced model may also include a function for computing the total calcium and total citrate at loc3 (FIG. 2), by considering mass flow balance between loc1 and loc3. The reduced model may further comprise one or more functions for computing the loss (clearance) of the respective form of calcium through the dialyzer membrane, as well as a function for predicting $CIT_{SYS}$ in the patient (cf. $f_3$). Based on the linear functions, the computation module 410 may be configured to compute, based on a measured value of $Ca_{SYS}$, the amount of the respective form of calcium in the patient's blood. Further, the module 410 may be configured to compute the amount of the respective form of calcium at loc3, compute and remove the respective loss through the dialyzer membrane, and sum the remaining amounts of the different forms of calcium to obtain the total calcium at loc2, i.e. $Ca_2$. The module 410 may also be configured to compute a current value of systemic total citrate ($CIT_{SYS}$), compute a corresponding amount of total citrate at loc3, compute and remove the loss of total citrate through the dialyzer membrane, to obtain the total citrate at loc2, i.e. $CIT_2$. The module 410 may then be configured to operate the linear function for ionized calcium on $Ca_2$ and $CIT_2$ to obtain $iCa_2$. If the measured value (402) instead represents $iCa_{SYS}$, the module 410 may be configured to operate the function $f_2$ on the measured $iCa_{SYS}$ value to obtain a computed $Ca_{SYS}$ value for use in the further computations.

The foregoing description is based on the assumption that the treatment protocol prescribes monitoring of ionized calcium downstream of the dialyzer, at loc2 in FIG. 2 (post-dialyzer ionized calcium). As mentioned in the Background section, the treatment protocol may alternatively, or additionally, prescribe that ionized calcium should be monitored upstream of the dialyzer, at loc3 in FIG. 2 (pre-dialyzer ionized calcium). As understood from the description of block 400 hereinabove (FIG. 4), the analysis for obtaining computation functions relevant to loc3 is a subset of the analysis for obtaining computation functions relevant to loc2. Thus, the foregoing teachings readily enable the skilled person to modify the predefined algorithm (used in computation block 410) to yield a computation value that represents ionized calcium, $iCa_3$, in blood at loc3, e.g. based on total calcium $Ca_3$ and total citrate $CIT_3$ at loc3, as indicated by a dashed box in FIG. 2. For example, with reference to FIG. 10, $f_{0,1}$ may be modified to define a functional relation between $iCa_3$ and $Ca_3$, $CIT_3$; $f_{0,2}$ may be modified to define a functional relation between $Ca_3$ and $Ca_{SYS}$; and $f_{0,3}$ may be modified to define a functional relation between $CIT_3$ and $CIT_{SYS}$. FIG. 11 is a flow chart of an example method 300' for performance monitoring of RCA during a blood treatment session based on pre-dialyzer ionized calcium. Steps 301'-304' correspond to steps 301-304 in FIG. 3 and need not be described in further detail.

Nomenclature

Alb: albumin concentration (mmol/L)
$HCO_3$: bicarbonate concentration (mmol/L)
$Ca_{REF}$: total calcium concentration at linearization reference point for loc2 (mmol/L)
$Ca_{REF\_2}$: total calcium concentration at linearization reference point for loc1 (mmol/l)
$Ca_x$: total calcium concentration at location x (mmol/L)
$Ca_{SYS}$: total calcium concentration in blood of patient (mmol/L)
$Ca_2$: total calcium concentration in blood at loc2 (mmol/L)
$Ca_3$: total calcium concentration in blood at loc3 (mmol/L)
$Ca_{PW2}$: total calcium concentration in plasma water at loc2 (mmol/L)
$CIT_{REF}$: total citrate concentration at linearization reference point for loc2 (mmol/L)
$CIT_{REF\_2}$: total citrate concentration at linearization reference point for loc1 (mmol/L)
$CIT_x$: total citrate concentration in blood at location x (mmol/L)
$CIT_2$: total citrate concentration in blood at loc2 (mmol/L)
$CIT_3$: total citrate concentration in blood at loc3 (mmol/L)
$CIT_{PBP}$: citrate concentration in citrate-containing fluid (mmol/L)
$CIT_{PW2}$: total citrate concentration in plasma water at loc2 (mmol/L)
$iCa_{SYS}$: ionized calcium concentration in blood of patient (mmol/L)
$iCa_2$: ionized calcium concentration in blood at loc2 (mmol/L)
$iCa_3$: ionized calcium concentration in blood at loc3 (mmol/L)
iCIT: ionized citrate concentration in blood of patient (mmol/L)
iP: ionized phosphate concentration in blood of patient (mmol/L)
$D_{CIT}$: citrate dose (mmol/L of blood)
$EQ_{CaHCO_3}$: equilibrium association constant for CaHCO3 (L/mmol)
$EQ_{CaCO_3}$: equilibrium association constant for CaCO3 (L/mmol)
$EQ_{CaP}$: equilibrium association constant for CaP (L/mmol)
$EQ_{CaCIT}$: equilibrium association constant for CaCit (L/mmol)
$EQ_{CaCIT2}$: equilibrium association constant for CaCit2 ($L^2/mmol^2$)
fwp: plasma water fraction
$F_{DIL}$: dilution ratio for plasma water when reaching dialyzer
$F_{CAL}$: fraction of patient plasma total calcium made available in plasma water for transfer through dialyzer membrane after citrate infusion.
$G_{MET}$: metabolic generation rate of citrate in the body of the patient (mmol/h)
H: hematocrit of patient blood as fraction of 1
$k_0A_Y$: mass transfer area coefficient of dialyzer for substance Y (mL/h)
$K_{BODY}$: plasma clearance of citrate in the body of the patient (L/h)
$K_Y$: plasma clearance of substance Y in the dialyzer (L/h)
$K_{Ca}$: plasma clearance of calcium in the dialyzer (L/h)
$K_{CIT}$ plasma clearance of citrate in dialyzer (L/h)
$Q_B$: blood flow rate from patient (mL/min)
$Q_D$: flow rate of dialysis fluid (mL/h)
$Q_E$: flow rate of effluent (mL/h)
$Q_{PW}$: plasma water flow rate (mL/h)
$Q_{PWI}$: plasma water flow rate at dialyzer inlet (mL/h)
$Q_{POST}$: flow rate of replacement fluid downstream of dialyzer (mL/h)
$Q_{PRE}$: flow rate of replacement fluid upstream of dialyzer (mL/h)
$Q_{PBP}$: flow rate of citrate-containing fluid (mL/h)

$Q_{FIL}$: ultrafiltration rate (mL/h)
t: time from start of RCA (h)
$V_D$: volume of citrate distribution (L)
W: weight of patient (kg)
$\alpha_Y$: Donnan factor

The invention claimed is:

1. A monitoring device for a blood treatment system, the blood treatment system comprising an extracorporeal blood circuit which comprises a blood withdrawal line and a blood return line for connection to a vascular system of a subject and a dialyzer intermediate the blood withdrawal and blood return lines, wherein the blood treatment system is configured for regional citrate anticoagulation by administration of citrate to the extracorporeal blood circuit upstream of the dialyzer during a treatment session, said monitoring device comprising:
a memory; and
a processor in communication with the memory, the processor configured to, at consecutive time steps during the treatment session:
obtain a current measurement value of systemic ionized calcium or systemic total calcium,
operate a predefined algorithm on the current measurement value to generate a current computation value that represents ionized calcium in blood at a selected location downstream or upstream of the dialyzer in the extracorporeal blood circuit, and
display, via a display device, the current computation value, and/or determine an assessment of the regional citrate anticoagulation based on the current computation value;
wherein the predefined algorithm comprises a first function configured to estimate the ionized calcium in the blood at the selected location in the extracorporeal blood circuit, said first function being linearly dependent on total calcium at the selected location and total citrate at the selected location.

2. The monitoring device of claim 1, wherein the processor is further configured to obtain input data comprising current values of operation parameters of the blood treatment system, and optionally one or more of system configuration data for the blood treatment system, chemical parameter data for substances in the blood, and physiological parameter data for the subject, wherein the processor is configured to operate the predefined algorithm on the input data and the current measurement value to generate the current computation value.

3. The monitoring device of claim 1, wherein the first function is obtained by linearization of a non-linear function with respect to each of total calcium and total citrate, wherein the non-linear function is a solution to a system of equations representing chemical reactions of calcium in free form and bound to other substances in blood, including citrate, while assuming predefined amounts of other substances than calcium and citrate.

4. The monitoring device of claim 3, wherein the linearization is performed with respect to reference values of total calcium and total citrate, said reference values corresponding to expected values of total calcium and total citrate, respectively, at the selected location.

5. The monitoring device of claim 1, wherein the predefined algorithm comprises a second function configured to estimate the total calcium in the blood at the selected location.

6. The monitoring device of claim 5, wherein the selected location is downstream of the dialyzer, and wherein the second function depends on the systemic total calcium and represents a mass balance of total calcium that enters the extracorporeal blood circuit in the blood from the subject and total calcium in the blood at an intermediate location in the extracorporeal blood circuit upstream of the dialyzer, while accounting for fluid infusion into the extracorporeal blood circuit intermediate the subject and the intermediate location, wherein the second function further accounts for a loss of total calcium from the blood in the dialyzer.

7. The monitoring device of claim 1, wherein the predefined algorithm comprises a third function configured to estimate the total citrate in the blood at the selected location in the extracorporeal blood circuit.

8. The monitoring device of claim 7, wherein the selected location is downstream of the dialyzer, wherein the third function depends on systemic total citrate and represents a mass balance of total citrate that enters the extracorporeal blood circuit in the blood from the subject and total citrate at an intermediate location in the extracorporeal blood circuit upstream of the dialyzer, while accounting for fluid infusion into the extracorporeal blood circuit intermediate the subject and the intermediate location, wherein the third function further accounts for a loss of total citrate from the blood in the dialyzer.

9. The monitoring device of claim 1, wherein the predefined algorithm further comprises a fourth function configured to estimate systemic total citrate as a function of time from start of the regional citrate anticoagulation.

10. The monitoring device of claim 9, wherein the fourth function represents a metabolic generation rate of citrate in the subject and further accounts for the administration of citrate into the extracorporeal blood circuit upstream of the dialyzer and a loss of total citrate from the blood in the dialyzer.

11. The monitoring device of claim 1, wherein the predefined algorithm further comprises at least one fifth function configured to estimate a clearance of total citrate and a clearance of total calcium from the blood in the dialyzer, wherein the processor is configured to compute a loss of total citrate and a loss of total calcium in the dialyzer based on the clearance of total citrate and the clearance of total calcium, respectively.

12. The monitoring device of claim 1, wherein the predefined algorithm comprises a sixth function configured to estimate systemic total calcium as a function of the systemic ionized calcium.

13. The monitoring device of claim 1, wherein the predefined algorithm comprises a seventh function configured to estimate the systemic ionized calcium as a function of the systemic total calcium.

14. The monitoring device of claim 1, wherein the current measurement value represents the systemic ionized calcium in the blood of the subject, wherein the processor is further configured to operate the predefined algorithm on the current measurement value to generate a further current computation value representing the systemic total calcium.

15. The monitoring device of claim 1, wherein the current measurement value represents the systemic total calcium, wherein the processor is further configured to operate the predefined algorithm on the current measurement value to generate a further current computation value representing the systemic ionized calcium.

16. The monitoring device of claim 1, wherein the processor is further configured to operate the predefined algorithm to generate a further current computation value representing systemic total citrate.

17. The monitoring device of claim 14, wherein the processor is further configured to evaluate at least the further current computation value for assessment of accumulation of citrate in the subject.

18. The monitoring device of claim 1, which further comprises an interface configured for signal communication with a blood analysis apparatus, wherein the processor is further configured to, at the respective consecutive time step, obtain the measurement value from a signal received over the interface from the blood analysis apparatus.

19. The monitoring device of claim 1, which is further configured to output the current computation value for presentation on a display device.

20. The monitoring device of claim 1, wherein the processor is further configured to evaluate the current computation value for detection of an alarm situation, and cause an alarm to be generated when the alarm situation is detected.

21. The monitoring device of claim 1, which further comprises a decision support module, which is configured to evaluate the current computation value in relation to a clinically proven protocol for the regional citrate anticoagulation, obtain a recommendation for operation of the blood treatment system based on the protocol, and output the recommendation for presentation on a display device.

22. The monitoring device of claim 1, which further comprises an interface configured for signal communication with a set of pumping devices in the blood treatment system, wherein the processor is further configured to generate one or more control signals for the set of pumping devices as a function of the current computation value, and provide the one of more control signals to the interface.

23. The monitoring device of claim 1, wherein the processor is further configured, during the treatment session, to obtain measurement data representing at least one of calcium and citrate in the blood of the subject and/or the extracorporeal blood circuit, and adjust the predefined algorithm based on the measurement data.

24. A blood treatment system comprising an extracorporeal blood circuit for connection to a vascular system of a subject, said extracorporeal blood circuit comprising a blood withdrawal line and a blood return line for connection to the vascular system, and a dialyzer intermediate the blood withdrawal and blood return lines, said blood treatment system further comprising a pumping device for pumping blood from the subject through the blood withdrawal line, the dialyzer and the blood return line back to the subject, said blood treatment system further comprising a sub-system which is operable to perform regional citrate anticoagulation in relation to the extracorporeal blood circuit and the subject, and a monitoring device in accordance with claim 1.

25. A method of monitoring a blood treatment system, the blood treatment system comprising an extracorporeal blood circuit which is configured for connection to a vascular system of a subject and comprises a dialyzer, wherein the blood treatment system is configured for regional citrate anticoagulation by administration of citrate to the extracorporeal blood circuit upstream of the dialyzer during a treatment session, said method comprising, at consecutive time steps during the treatment session:
  obtaining a current measurement value of systemic ionized calcium or systemic total calcium,
  operating a predefined algorithm on the current measurement value to generate a current computation value representing ionized calcium in blood at a selected location downstream or upstream of the dialyzer in the extracorporeal blood circuit, wherein the predefined algorithm comprises a first function configured to estimate the ionized calcium in the blood at the selected location in the extracorporeal blood circuit, said first function being linearly dependent on total calcium at the selected location and total citrate at the selected location, and
  displaying, via a display device, the current computation value, and/or determining an assessment of the regional citrate anticoagulation based on the current computation value.

26. A non-transitory, computer-readable medium storing computer instructions which, when executed by a processor, cause the processor to:
  obtain a current measurement value of systemic ionized calcium or systemic total calcium;
  operate a predefined algorithm on the current measurement value to generate a current computation value representing ionized calcium in blood at a selected location downstream or upstream of a dialyzer in a extracorporeal blood circuit, wherein the predefined algorithm comprises a first function configured to estimate the ionized calcium in the blood at the selected location in the extracorporeal blood circuit, said first function being linearly dependent on total calcium at the selected location and total citrate at the selected location; and
  display, via a display device, the current computation value, and/or determine an assessment of the regional citrate anticoagulation based on the current computation value.

* * * * *